United States Patent
Genkin et al.

(10) Patent No.: US 9,463,223 B2
(45) Date of Patent: Oct. 11, 2016

(54) METHOD FOR MONITORING DEVELOPMENT OF SOMATIC MOSAICISM

(71) Applicant: CLS Therapeutics Limited, Gurnsey, Channel Islands (GB)

(72) Inventors: Dmitry Dmitrievich Genkin, Saint-Petersburg (RU); Georgy Viktorovich Tets, Saint-Petersburg (RU); Viktor Veniaminovich Tets, Saint-Petersburg (RU)

(73) Assignee: CLS Therapeutics Limited, St. Peter Port, Guernsey, Channel Islands (GB)

(*) Notice: Subject to any disclaimer, the term of this patent is extended or adjusted under 35 U.S.C. 154(b) by 204 days.

(21) Appl. No.: 14/309,363

(22) Filed: Jun. 19, 2014

(65) Prior Publication Data

US 2015/0010523 A1     Jan. 8, 2015

Related U.S. Application Data

(63) Continuation of application No. 13/772,499, filed on Feb. 21, 2013, now Pat. No. 8,796,004, which is a continuation of application No. 12/835,029, filed on Jul. 13, 2010, now Pat. No. 8,388,951, which is a continuation-in-part of application No. 10/564,609, filed as application No. PCT/RU2004/000260 on Jul. 1, 2004, now abandoned.

(30) Foreign Application Priority Data

Jul. 14, 2003   (RU) ................ PCT/RU2003/000304
Mar. 12, 2004   (RU) ........................ RU2004108057

(51) Int. Cl.
| C12Q 1/68 | (2006.01) |
| A61K 38/46 | (2006.01) |
| C12N 9/22 | (2006.01) |

(52) U.S. Cl.
CPC .......... *A61K 38/465* (2013.01); *C12Q 1/6883* (2013.01); *C12Y 301/21001* (2013.01); *C12Q 2600/156* (2013.01)

(58) Field of Classification Search
CPC .............. A61K 38/465; C12Q 1/6883; C12Q 2600/156; C12Y 301/21001
See application file for complete search history.

(56) References Cited

U.S. PATENT DOCUMENTS

| 4,485,095 A | 11/1984 | Fujisaki et al. |
| 5,484,589 A | 1/1996 | Salganik |
| 5,656,589 A | 8/1997 | Stossel et al. |
| 5,889,153 A | 3/1999 | Suzuki et al. |
| 5,952,170 A | 9/1999 | Stroun et al. |
| 6,033,846 A | 3/2000 | Fournie |
| 6,156,504 A | 12/2000 | Gocke et al. |
| 6,391,607 B1 | 5/2002 | Lazarus et al. |
| 6,428,785 B1 | 8/2002 | Gokeen |
| 6,455,250 B1 | 9/2002 | Aguilera et al. |
| 6,465,177 B1 | 10/2002 | Hoon |
| 6,521,409 B1 | 2/2003 | Gocke et al. |
| 7,612,032 B2 | 11/2009 | Genkin et al. |
| 2003/0044403 A1 | 3/2003 | Shak |
| 2004/0001817 A1 | 1/2004 | Giampapa |
| 2004/0157239 A1 | 8/2004 | Tanuma et al. |
| 2006/0228347 A1 | 10/2006 | Sunaga et al. |
| 2006/0233780 A1 | 10/2006 | Genkin et al. |
| 2008/0004561 A1 | 1/2008 | Genkin et al. |
| 2009/0047272 A1 | 2/2009 | Appelbaum et al. |
| 2009/0053200 A1 | 2/2009 | Genkin et al. |
| 2010/0061971 A1 | 3/2010 | Genkin et al. |
| 2010/0150903 A1 | 6/2010 | Genkin et al. |
| 2011/0033438 A1 | 2/2011 | Bartoov et al. |
| 2011/0070201 A1 | 3/2011 | Shaaltiel et al. |
| 2011/0189156 A1 | 8/2011 | Genkin et al. |

FOREIGN PATENT DOCUMENTS

| CA | 2394856 | 6/2001 |
| CA | 2184582 | 12/2001 |
| DE | 4024530 | 2/1992 |
| DE | 10221194 | 12/2003 |
| EP | 0325191 | 7/1989 |
| EP | 1431762 A1 | 6/2004 |
| EP | 1655036 | 5/2006 |
| EP | 1880733 | 1/2008 |
| EP | 2095825 | 6/2011 |
| GB | 984464 | 2/1965 |
| GB | 1005985 | 9/1965 |
| JP | 61293927 | 12/1986 |
| JP | 2006-290769 | 10/2006 |
| NZ | 299257 | 8/2000 |
| RU | 2099080 | 12/1997 |

(Continued)

OTHER PUBLICATIONS van der Vaart et al., Annals of the New York Academy of Science 1137:92-97, 2008.*
Beishon, M., CancerWorld Sep.-Oct. 2015: 12-17.*
Anker, P. et al., Tumor-related alterations in circulating DNA, potential for diagnosis, prognosis and detection of minimal residual disease, Leukemia, 15, 289-91, 2001.
Ashton, G., Growing pains for biopharmaceuticals, Nature Biotech, vol. 19, pp. 307-311, 2001.
Aung et al., Current status and future potential of somatic mutation testing from circulating free DNA in patients with solid tumours, Hugo J, vol. 4, pp. 11-21, 2010.

(Continued)

*Primary Examiner* — Delia Ramirez
(74) *Attorney, Agent, or Firm* — Troutman Sanders LLP

(57) ABSTRACT

The invention is directed to treatment of systemic DNA mutation diseases accompanied with development of somatic mosaicism and elevation of blood extracellular DNA. The inventive method comprises introducing a DNASE enzyme into the systemic blood circulation of a patient in doses and regimens which are sufficient to decrease average molecular weight of circulating extracellular blood DNA in the blood of said patient.

5 Claims, 2 Drawing Sheets

(56) References Cited

FOREIGN PATENT DOCUMENTS

| | | |
|---|---|---|
| RU | 2001104426 | 1/2003 |
| RU | 2202109 | 4/2003 |
| RU | 2207876 | 7/2003 |
| RU | 2239404 | 11/2004 |
| RU | 2239442 | 11/2004 |
| RU | WO2005/007187 | 1/2005 |
| RU | 2267329 | 1/2006 |
| RU | 2269356 | 2/2006 |
| RU | 2269357 | 2/2006 |
| RU | 2269359 | 2/2006 |
| RU | 2308968 | 10/2007 |
| WO | WO93/03709 | 3/1993 |
| WO | WO95/00170 | 1/1995 |
| WO | WO97/28266 | 8/1997 |
| WO | WO97/47751 | 12/1997 |
| WO | WO00/03709 | 1/2000 |
| WO | WO00/31238 | 6/2000 |
| WO | WO01/74905 | 10/2001 |
| WO | WO03/068254 | 8/2003 |
| WO | WO2005/004903 | 1/2005 |
| WO | WO2005/004904 | 1/2005 |
| WO | EP1666055 | 2/2005 |
| WO | WO2005/115444 | 12/2005 |
| WO | WO2006/130034 | 12/2006 |
| WO | WO2008/047364 | 4/2008 |
| WO | WO2008/066403 | 6/2008 |
| WO | WO2011/073665 | 6/2011 |
| WO | WO2012/075506 | 6/2012 |

OTHER PUBLICATIONS

Botto, N., et al., Elevated levels of oxidative DNA damage in patients with coronary artery disease, Coronary Artery Disease, vol. 13, pp. 269-274, 2002.
Boyko et al., Cell-free DNA—a marker to predict ischemic brain damage in a rat stroke experimental model, Journal of Neurosurgical Anesthesiology, vol. 23, pp. 222-228, 2011.
Burt et al., Detection of circulating donor deoxyribonucleic acid by microsatellite analysis in a liver transplant recipient. Liver Transpl Surg. (2), pp. 391-394, 1996.
Davis JC et al., Recombinant human Dnase I (rhDNase) in patients with lupus nephritis, LUPUS, vol. 8, pp. 68-76, 1999.
Davis, Brian R. et al., Somatic mosaicism in the Wiskott—Aldrich syndrome: Molecular and functional characterization of genotypic revertants, Clinical Immunology, vol. 135, pp. 72-83, 2010.
Dayan, Pharmacological-Toxicological (Expert Report on Recombinant Human Deoxyribonuclease I (rhDNase; PulmozymeTM) , Hum. Exp. Toxicol., 13: S2, 1994.
Deitsch, et al., Transformation of malaria parasites by the spontaneous uptake and expression of DNA from human erythrocytes, Nucleic Acids Research, vol. 29, pp. 850-853, 2000.
Deocharan B., et al., Alpha-actinin is a cross-reactive renal target for pathogenic anti-DNA antibodies, J. Immunol., vol. 168, pp. 3072-3078, 2002.
Department of Health and Human Services Food and Drug Administration, Federal Register, Dec. 13, 1985, vol. 50, No. 240.
Dittmar, Manuela el al. A novel mutation in the *DNASE1* gene is related with protein instability and decreased enzyme activity in thyroid autoimmunity, Journal of Autoimmunity, vol. 32, pp. 7-13, 2009.
El Hassan No, et al. Rescue use of Dnase in critical lung atelectasis mucus retention in premature neonates, Pediatrics., vol. 108, pp. 468-470, 2001.
Erickson, Robert P., Somatic gene mutation and human disease other than cancer, Mutation Research, vol. 543, pp. 125-136, 2003.
Erickson, Robert P., Somatic gene mutation and human disease other than cancer: An update, Mutation Research, vol. 705, pp. 96-106, 2010.
Extended European Search Report for European Patent Appl. No. EP12170750 dated Aug. 3, 2012.
Extended European Search Report for European Patent Appl. No. EP12170754 dated Aug. 3, 2012.
Extended European Search Report for European Patent Appl. No. EP12170757 dated Aug. 3, 2012.
Favorov, P.V. Issledovaniye kinetiki prevrashchenii DNK pod deistviem DNK-topoizomeraz i DNK-abzimov, author's abstract of PhD thesis in biological sciences, M., pp. 3-4, 1999 (Reference in Russian and English-language translation).
Freshney, R. I., Culture of Animal Cells, A Manual of Basic Technique, Alan R. Liss, Inc., New York, pp. 3-4, 1983.
Funakoshi, A, et al., Clinical Investigation of Serum Deoxyribonuclease: II. Clinical Studies of Serum Deoxyribonuclease Activity in Pancreatic Disease, Gastroenterologia Japonica, vol. 14, pp. 436-440, 1979.
Gannushikina, I.V., et al., Plasma DNA Levels in Patients with Atherosclerotic Involvement of the Major Arteries of the Head and lateral Amyotrophic Sclerosis, Bulletin of Experimental Biology and Medicine, vol. 124, No. 12, pp. 1164-1166, 1997 (Translated from: Gannushkina I. V. et al., Uroven DNK v plazme krovi bolnykh s 1-4 ateroskleroticheskim porazheniem magistralnykh artery golovy i bokovym amiotroficheskim sklerozom Byulleten' Experimental'noi Biologii i Meditsiny, Moscow, Meditsina, No. 12, pp. 610-612, 1997).
Gannushkina I.V. et al., Uroven DNK v plazme krovi bolnykh s 1-4 ateroskleroticheskim porazheniem magistralnykh artery golovy i bokovym amiotroficheskim sklerozom Bjulleten experimentalnoi biologii i meditsiny. Moscow, Meditsina, No. 12, pp. 610-612, 1997.
Gibbs et al., Mechanism-Based Target Identification and Drug Discovery in Cancer Research Science, vol. 287, pp. 1969-1973, 2000.
Gluhov BM, Znachenije nukleaz v patogeneze neirovirusnyh zabolevanij, Avtoreferat dissertatsii na soiskanie uchenoi stepeni doktora medicinskikh nauk (author's abstract of MD thesis in medical sciences), Novosibirsk, pp. 15-16, 21-26, 1996 (Reference in Russian and English-language translation of pp. 14-17 and 20-27).
Gormally et al., Circulating free DNA in plasma or serum as biomarker of carcinogenesis: Practical aspects and biological significance, Mutation Research, vol. 635, pp. 105-117, 2007.
Gorrini, C., et al., Effect of apoptogenic stimuli on colon carcinoma cell lines with a different c-myc expression level, Int J Mol Med, vol. 11, pp. 737-742, 2003.
Gura, T., Systems for Identifying New Drugs Are Often Faulty, Science, vol. 278, pp. 1041-1042, 1997.
Hann, et al. Building 'validated' mouse models of human cancer. Curr Opin Cell Biol, 13(6), pp. 778-784, 2001.
Holterhus, Paul-Martin et al., Mosaicism due to a Somatic Mutation of the Androgen Receptor Gene Determines Phenotype in Androgen Insensitivity Syndrome, Journal of Clinical Endocrinology and Metabolism, vol. 82, No. 11, pp. 3584-3589, 1997.
Horlitz, Martin et al., Optimized Quantification of Fragmented, Free Circulating DNA in Human Blood Plasma Using a Calibrated Duplex Real-Time PCR, PLoS ONE, vol. 4, Issue 9, e7207, 2009.
Huttunen, R., et al., Fatal Outcome in Bacteremia is Characterized by High Plasma Cell Free DNA Concentration and Apoptotoc DNA Fragmentation: A Prospective Cohort Study, PLoS ONE, vol. 6, e21700, 2011.
International Search Report for PCT/RU2003/000304, mailed on Mar. 25, 2004.
International Search Report for PCT/RU2004/000260, mailed on Dec. 9, 2004.
International Search Report for PCT/RU2004/000261, mailed on Oct. 21, 2004.
International Search Report for PCT/RU2004/000262, mailed on Oct. 21, 2004.
International Search Report for PCT/RU2005/000236, mailed on Nov. 24, 2005.
International Search Report for PCT/RU2006/000642, mailed on Aug. 2, 2007.
Ju Ncosa, Barbara, DNA on the Loose: Next-Gen Blood Tests Tap Free-Floating Genetic Material, Scientific American, Mar. 18, 2009.

(56) References Cited

OTHER PUBLICATIONS

Jylhava et al., Aging is associated with quantitative and qualitative changes in circulating cell-free DNA: the Vitality 90+ study, Mechanisms of Ageing and Development, vol. 132, pp. 20-26, 2011.
Kalandarishvili F., Nakoplenie spontanno povrezhdennoj DNK v ne- i postgepatjektomirovannoj pecheni u staryh krys, Med. Novosti Gruzii, No. 5, pp. 11-12, 1998 (Reference in Russian and English-language translation).
Kaprin et al., Prognoz i lechenie bol'nih poverhnostnim rakom mochevogo puziria visokoi stepeni riska, Visokie Tehnologii v Onkologii, Rostov-na-Donu, vol. 3, pp. 149-150, 2000 (reference in Russian and English-language translation).
Kawane, K, et al., DNAse II deficiency causes chronic polyarthritis in mice, Nature Clinical Practice Rheumatology, vol. 3, No. 4, p. 192, 2007.
Krapf F. et al., The estimation of circulating immune complexes, C3d, and anti-ds-DNA-antibody serum levels in the monitoring of therapeutic plasmapheresis in a patient with systemic lupus erythematosus. A case report, Clin Exp Rheumatol., vol. 3, pp. 159-162, 1985.
Lachmann PJ, Lupus and Desoxyribonuclease, Lupus, vol. 12, pp. 202-206, 2003.
Lecompte, et al., Detection of free-circulating tumor-associated DNA in plasma of colorectal cancer patients and its association with prognosis, Int. J. Cancer, vol. 100, pp. 542-548, 2002.
Lee, D., Continued Marketing of a Useless Drug ('Varidase') in Panama, Lancet, Mar., vol. 335, p. 667, 1990.
Leland et al., Cancer chemotherapy—ribonucleases to the rescue, Chem. & Bio., vol. 8, pp. 405-413, 2001.
Leon et al., Free DNA in the Serum of Cancer Patients and the Effect of Therapy, Cancer Research, vol. 37, pp. 646-650, 1977.
Li et al., The *Haemophilus ducreyi* cytolethal distending toxin activates sensors of DNA damage and repair complexes in proliferating and non-proliferating cells, Cellular Microbiology, vol. 4, pp. 87-99, 2002.
Liggett et al. , Methylation patterns of cell-free plasma DNA in relapsing-remitting multiple sclerosis, Journal of Neurological Sciences, vol. 290, pp. 16-21, 2010.
Macanovic et al., The treatment of systemic lupus erythematosus (SLE) in NZB/W F1 hybrid mice; studies with recombinant murine DNase and with dexamethasone. Clinical and Experimental Immunology (106), pp. 243-252, 1996.
Malickova, Karin et al., Decreased Activity of DNase-I Predisposes to Immune-Mediated Complications in IBD Patients During Anti-TNFA Treatment, Gastroenterology, Abstract 202, vol. 138 (5 Supplement 1), S-37, 2010.
Maurer, HR, Bromelain: biochemistry, pharmacology and medical use, Cell Mol. Life. Sci., vol. 58, pp. 1234-1245, 2001.
Mel'Nikov D, Voprosy onkologicheskoi pomoschi na etape reformirovaniya zdravookhraneniya, Ekaterinburg, pp. 159-161, 1996 (Reference in Russian and English-language translation).
Merkus et al., DNase treatment for atelectasis in infants with severe respiratory syncytial virus bronchiolitis, Eur Respir J, vol. 18, pp. 734-737, 2001.
Moreira VG et al., Usefulness of cell-free plasma DNA, procalcitonin and C-reactive protein as markers of infection in febrile patients, Annals of Clinical Biochemistry, vol. 47, pp. 253-258, 2010.
Mosca et al., Cell-free DNA in the plasma of patients with systemic sclerosis, Clinical Rheumatology, vol. 28, pp. 1437-1440, 2009.
Mutirangura A., Serum/plasma viral DNA: mechanisms and diagnostic applications to nasopharyngeal an cervical carcinoma, Ann NY Acad Sci., vol. 945, pp. 59-67, 2001.
Nestle & Roberts, An extracellular nuclease from Serratia marcescens, J. Biol. Chem., vol. 244, pp. 5213-5218, 1969.
Ngan et al., Remarkable Application of Serum EBV EBER-1 in Monitoring Response of Nasopharyngeal Cancer Patients to Salvage Chemotherapy, Ann. NY Acad. Sci., vol. 945, pp. 73-79, 2001.
Nikolenko G. N., Sozdanie rekombinantnykh antitel 17 protiv virusa kleschevogo entsefalita i izuchenie ikh svoystv, Avtoreferat dissertatsii na soiskanie uchenoi stepeni kandidata biologicheskikh nauk (author's abstract of PhD thesis in biological sciences), Koltsovo, pp. 1-2, 19, 1999 (Reference in Russian and English-language translation).
Oliven et al., Orally and Rectally Administered Streptokinase, Pharmacology, vol. 22, pp. 135-138, 1981.
Osivac et al., Reorganizacija DNK i biologicheskoje starenije, Biohimija, vol. 62, pp. 1491-1502, 1997 (Reference in Russian and English-language translation).
Perel'Man Mi, et al., Molekuljarnaja medicina i lechenie tuberkuleza, Problemi tuberkuleza, No. 5, pp. 5-7, 2001 (Reference in Russian and English-language translation).
Pisetsky, D., Immune response to DNA in systemic lupus erythematosus, Isr. Med. Assoc. J., vol. 3, pp. 850-853, 2001.
Pressler T., Review of recombinant human deoxyribonuclease (rhDNase) in the management of patients with cystic fibrosis, Biologics: Targets & Therapy, vol. 2, pp. 611-617, 2008.
Prince, W.S., et al, Pharmacodynamics of recombinant human DNase I in serum, Clin Exp Immunol, vol. 113, pp. 289-296, 1998.
Pulmozyme® (dornase alfa) Inhalation Solution product leaflet, Genetech, Inc., 2005.
Rao KS and Shrivastaw KP, Studies on the synthesis and degradation of DNA in developing and old chick cerebellum, Journal of Neurochemistry, vol. 27, pp. 1205-1210, 1976.
Raz E. et al., Anti-DNA antibodies bind directly to renal antigens and induce kidney dysfunction in the isolated perfused rat kidney, J Immunol., vol. 142, pp. 3076-3082, 1989.
Ross, Kenneth Andrew, Evidence for somatic gene conversion and deletion in bipolar disorder, Crohn's disease, coronary artery disease, hypertension, rheumatoid arthritis, type-1 diabetes, and type-2 diabetes, BMC Medicine, vol. 9, No. 12, pp. 1-29, 2011.
Roche, Pulmozyme®, Dornase alfa solution for inhalation 1.0 mg/ml, Data Sheet, 2008.
Schapira, Anthony H. V., Mitochondrial disease, Lancet, vol. 368, pp. 70-82, 2006.
Sergeeva L. M., Kliniko-laboratonaya otsenka mukoliticheskogo effekta pulmozima u bolnykh mukovistsidozom, Ekaterinburg, 1999, PhD dissertation in medicine, p. 9, paragraphs 2-3; p. 12, paragraph 4; p. 13, paragraphs 1-2; p. 17, paragraph 4; p. 18, paragraph 1; p. 30, paragraphs 3-4; p. 31, paragraph 2 (Reference in Russian and English Translation).
Shak et al., Recombinant human DNAse I reduces the viscosity of cystic fibrosis sputum, Proc. Natl. Acad. Sci. USA, vol. 87, pp. 9188-9192, 1990.
Sherry et al., Presence and Significance of Desoxyribose Nucleoprotein in the Purulent Pleural Exudates of Patients, Proc, Soc. Exp. Biol. Med., pp. 179-184, 1948.
Shfvchuk, N.A., Vrornyarazreshermiy Immunofluorcseentniy Analiz na DNK i Issiodovanie Soderzhaniya DNK v Syvorotke Cheloveka, Voprosi Medicinskoi Khimii, No. 4, 2001 (Reference in Russian and English Translation).
Shimony et al., Cell free DNA detected by a novel method in acute ST-elevation myocardial infarction patients, Acute Cardiac Care, vol. 12, pp. 109-111, 2010.
SIGMA Product Information sheet for Deoxyribonuclease I from Bovine Pancreas.
Simpson G., et al., Successful treatment of empyema thoracis with human recombinant deoxyribonuclease, Thorax, vol. 58, pp. 365-366, 2003.
Sugihara et al., Deoxyribonuclease treatment prevents blood-borne lier metastasis of cutaneously transplanted tumour cells in mice, Br. J. Cancer (67), pp. 66-70, 1993.
Supplementary European Search Report for European Patent Appl. No. EP06843990, dated Nov. 23, 2009 and cf Form 1507.
Supplementary European Search Report for European Patent Appl. No. EP04748955, mailed May 19, 2009.
Supplementary European Search Report for European Patent Appl. No. EP04775224, mailed Oct. 28, 2009.
Supplementary European Search Report for European Patent Appl. No. EP05745412, dated Jul. 10, 2009.
Supplementary European Search Report for European Patent Appl. No. EP03796243, dated Jan. 12, 2010.

(56) References Cited

OTHER PUBLICATIONS

Tetz VV and Tetz GV, Effect of Extracellular DNA Destruction by DNase I on Characteristics of Forming Biofilms, DNA and Cell Biology, vol. 29, pp. 399-405, 2010.

Tetz, GV, et al., Effect of DNase and Antibiotics on Biofilm Characteristics, Antimicrobial Agents and Chemotherapy, vol. 53, pp. 1204-1209, 2009.

Tetz, GV, et al., Effect of nucleolytic, proteolytic, and lipolytic enzymes on transfer of antibiotic resistance genes in mixed bacterial communities, Universal Journal of Medicine and Dentistry, vol. 1, pp. 46-50, 2012.

Translation of International Preliminary Report on Patentability for PCT/RU2003/000304, dated Nov. 1, 2005.

Translation of International Preliminary Report on Patentability for PCT/RU2004/000260, mailed Jan. 14, 2006.

Translation of International Preliminary Report on Patentability for PCT/RU2004/000261, mailed Dec. 2, 2005.

Translation of International Preliminary Report on Patentability for PCT/RU2004/000262, mailed Apr. 12, 2006.

Translation of International Preliminary Report on Patentability for PCT/RU2005/000236, mailed Feb. 13, 2008.

Translation of International Preliminary Report on Patentability for PCT/RU2006/000642, dated Jul. 7, 2009.

Ulrich & Friend, Toxicogenomics and drug discovery: will new technologies help us produce better drugs? Nature, vol. 1, pp. 84-88, 2002.

Varidase Buccal Tablets product information from Lederle Laboratories Inc., Canad. M. A. J., vol. 84, pp. 867-868, 1961.

Varidase product information from EPGOnline, accessed on Dec. 12, 2011.

Vonmoos, P.L. and Straub, P.W., Absorption and hematologic effect of streptokinase-streptodornase (varidase) after intracavital or oral administration, Schweiz Med Wochenschr, vol. 109, pp. 1538-1544, 1979, Abstract.

Whitchurch, et al., Extracellular DNA Required for Bacterial Biofilm Formation, Science, vol. 295, p. 1487, 2002.

Yastrebova N.E., Razrabotka i izuchenie diagnosticheskikh vozmozhnostei immunofermentnykh test-sistem na osnove antigen-nykh preparatov zolotistogo stafilokokka i DNK, Avtoreferat dissertatsii na soiskanie uchenoi stepeni kandidata meditsinskikh nauk (author's abstract of PhD thesis in medical sciences), M., pp. 17-18, 1988 (Reference in Russian and English-language translation).

Yasuda, Toshihiro et al., Activity Measurement for Deoxyribonucleases I and II with Picogram Sensitivity Based on DNA/SYBR Green I Fluorescence, Analytical Biochemistry, vol. 255, pp. 274-276, 1998.

Ye et al., Quantification of Circulating Cell-Free DNA in the Serum of Patients with Obstructive Sleep Apnea-Hypopnea Syndrome, Lung, vol. 188, pp. 469-474, 2010.

Zaman, et al., Direct amplification of Entamoeba histolytica DNA from amoebic liver abscess pus using polymerase chain reaction, Parasitol. Res., vol. 86, pp. 724-728, 2000.

Zaravinos et al., Levosimendan reduces plasma cell-free DNA levels in patients with ischemic cardiomyopathy, J. Thromb. Thrombolysis, vol. 31, pp. 180-187, 2011.

Zhong et al., Presence of mitochondrial tRNA(leu(UUR) a to G 3243 mutation in DNA extracted from serum and plasma of patients with type A 2 diabetes mellitus. J. Clin. Pathol., vol. 53, pp. 466-469, 2000.

\* cited by examiner

METHOD FOR MONITORING DEVELOPMENT OF SOMATIC MOSAICISM

CROSS-REFERENCE TO RELATED APPLICATIONS

This application is a Continuation of U.S. application Ser. No. 13/772,499 filed Feb. 21, 2013, which is a Continuation of U.S. application Ser. No. 12/835,029 filed Jul. 13, 2010, now U.S. Pat. No. 8,388,951, which is a Continuation-in-Part of U.S. application Ser. No. 10/564,609 filed Jan. 12, 2006, which is a U.S. national phase application under 35 U.S.C. §371 of International Patent Application No. PCT/RU2004/000260, filed Jul. 1, 2004 (published in Russian on Jan. 20, 2005 as WO 2005/004789), which claims priority of Russian Federation Patent Application No. RU2004108057, filed Mar. 12, 2004 and International Patent Application No. PCT/RU2003/000304 filed Jul. 14, 2003, all of which are incorporated by reference as if fully rewritten herein.

SEQUENCE LISTING

The instant application contains a Sequence Listing which has been submitted electronically in ASCII format and is hereby incorporated by reference in its entirety. Said ASCII copy, created on Sep. 16, 2014, is named 243736.000083_SL.txt and is 59,899 bytes in size.

BACKGROUND OF THE INVENTION

1. Field of the Invention

The present invention relates generally to medical treatment of the systemic DNA mutation diseases accompanied with development of somatic mosaicism and elevation of blood extracellular DNA and, more particularly, to a treatment of diabetes mellitus and atherosclerosis.

2. Description of the Related Art

Mosaicism refers to a mixture of cells of different genetic composition in one individual. When DNA mutation is detectable in number, but not all somatic cells in one individual, it is called somatic mosaicism. Development of somatic mosaicism has been recently recognized as important mechanism of systemic DNA mutation diseases progression (Gottlieb B et al., Selection and mutation in the "new" genetics: an emerging hypothesis, Hum Genet. 2010 March; 127(5): 491-501.) Importance of somatic mosaicism involving disease-causing mutations has been reported for variety of monogenic (reviewed by Youssoufian H., Nature Reviews Genetics 3, 748-758, October 2002) and more recently for multifactor DNA mutation diseases: cardiac rhythm disorders (M. H. Gollob et al., Somatic mutations in the connexin 40 gene (GJA5) in atrial fibrillation, N. Eng. J. Med. 354 (2006), pp. 2677-2688.); atherosclerosis (S. De Flora et al., Mutagenesis and cardiovascular diseases. Molecular mechanisms, risk factors, and protective factors, Mutat. Res. 621 (2007), pp. 5-17), systemic vascular disorders (B. Gottlieb et al., BAK1 gene variation and abdominal aortic aneurysms, Hum. Mutat. 30 (2009), pp. 1043-1047); immune deficiencies (Wada T. et al., Somatic mosaicism in primary immune deficiencies, Curr Opin Allergy Clin Immunol. 2008 December; 8(6): 510-4); Alzheimer disease (Beck J A et al., Somatic and germline mosaicism in sporadic early-onset Alzheimer's disease. Hum Mol Genet. 2004 Jun. 15; 13(12): 1219-24.); diabetes mellitus (Emma L. Edghill et al, Origin of de novo KCNJ11 mutations and risk of neonatal diabetes for subsequent siblings. The Journal of Clinical Endocrinology & Metabolism Vol. 92, No. 5 1773-1777).

According to current knowledge the systemic DNA mutation diseases represent very distinct subsets of human pathology different in etiology and pathogenesis and accordingly has fundamentally different, usually palliative treatment modalities—cholesterol lowering therapy for atherosclerosis (New Concepts and Paradigms in Cardiovascular Medicine: The Noninvasive Management of Coronary Artery Disease, K. Lance Gould, THE AMERICAN JOURNAL OF MEDICINE, Volume 104, Jun. 22, 1998, pp. 2-17) and insulin therapy or insulin sensitization therapy for diabetes mellitus (Pharmacological Management of Diabetes: Recent Progress and Future Perspective in Daily Drug Treatment, Gerard Emilien et al., Pharmacol. Ther. Vol. 81, No. 1, pp. 37-51, 1999).

More recently the gene therapy was recognized as potential tool for disease specific intervention which may target the function of certain specific disease involved genes and provide more efficient cure based on repair of existing genetic defects in atherosclerosis (Ishisaki A, et al., Novel ideas of gene therapy for atherosclerosis: modulation of cellular signal transduction of TGF-beta family. Curr Pharm Des. 2006; 12(7): 877-86; Harris J D, et al. ApoE gene therapy to treat hyperlipidemia and atherosclerosis. Curr Opin Mol Ther. 2006 August; 8(4): 275-87; Hayden et al. Gene therapy method for reducing risk of atherosclerosis, U.S. Pat. No. 6,784,162) and diabetes mellitus (G B Parsons, Ectopic expression of glucagon-like peptide 1 for gene therapy of type II diabetes, Gene Therapy (2007) 14, 38-48; L. Chan, In vivo gene therapy for diabetes mellitus, Trends in Molecular Medicine, Volume 9, Issue 10, October 2003, Pages 430-435; M. During, Compositions for gene therapy of diabetes, EP1889914).

However no cure exists which may target the evolution of disease causing DNA mutations leading to development of somatic mosaicism. Accordingly, the development of new effective, non-toxic method that may suppress the development of somatic mosaicism and consequently be effective cure for systemic DNA mutation disease is an extremely important task.

Circulating extracellular nucleic acids were discovered more than 60 years ago (Anker P Circulating DNA in plasma or serum, Clin Chim Acta. 2001 November; 313(1-2): 143-6). However until now elevated levels of extracellular blood DNA in systemic DNA mutation diseases, and in particular in atherosclerosis and diabetes mellitus were considered only as useful diagnostic and research tool (EI Tarhouny S. A. et al., Assessment of cell-free DNA with microvascular complication of type II diabetes mellitus, using PCR and ELISA. Nucleosides Nucleotides Nucleic Acids. 2010 March; 29(3): 228-36; Langford M P et al., Plasma levels of cell-free apoptotic DNA ladders and gamma-glutamyltranspeptidase (GGT) in diabetic children. Exp Biol Med (Maywood). 2007 October; 232(9): 1160-9; Amalich F. et al., Prognostic value of cell-free plasma DNA in patients with cardiac arrest outside the hospital: an observational cohort study, Critical Care 2010, 14; Amalich F. Association of cell-free plasma DNA with preoperative mortality in patients with suspected acute mesenteric ischemia, Clinica Chimica Acta, in press; Zhong S, Presence of mitochondrial tRNA (Leu (UUR)) A to G 3243 mutation in DNA extracted from serum and plasma of patients with type 2 diabetes mellitus 2000 June; 53(6): 466-9.)

Circulating extracellular nucleic acids have never been considered as potential therapeutic target in systemic DNA mutation diseases. Accordingly, no therapeutic method was developed which targets extracellular blood DNA in systemic DNA mutation diseases. Thus it makes impossible to take any technical solution as prototype.

As used in this application, the following terms are meant to have the following corresponding definitions.

Deoxyribonuclease (DNASE) is any enzyme that catalyzes the hydrolytic cleavage of phosphodiester linkages in the DNA backbone.

Extracellular blood DNA number average molecular weight—the number average molecular weight is a way of determining the molecular weight of a polymer. The number average molecular weight is the ordinary arithmetic mean or average of the molecular weights of the individual DNA macromolecules. It is determined by measuring the molecular weight of n polymer molecules, summing the weights, and dividing by n. The number average molecular weight of extracellular blood DNA can be determined by gel electrophoresis. The shift of extracellular blood DNA bands to low-MW areas reflect decrease number average molecular weight and in fact reflects enzymatic cleavage of extracellular blood DNA.

DNA mutation disease refers to diseases where specific DNA mutation has been identified as single leading cause (monogenic or single gene disorders) or multifactor disorders resulting from mutations in multiple genes, often coupled with environmental causes.

Systemic disease is one that affects a number of organs and tissues, or affects the body as a whole.

SUMMARY OF THE INVENTION

The object of this invention is to develop high-performance and low-toxic method for treatment of systemic DNA mutation diseases accompanied with development of somatic mosaicism and elevation of blood extracellular DNA and, more particularly, to a treatment of diabetes mellitus and atherosclerosis.

According to the invention this task is resolved by introducing a treatment agent into a circulating blood system of a patient diagnosed with systemic DNA mutation disease when said treatment agent destroys extracellular DNA in said blood of said patient and wherein said treatment agent used to destroy said extracellular DNA is a DNASE enzyme. In one of preferred embodiments said agent must be administered in doses and regimens which sufficient to decrease number average molecular weight of circulating extracellular blood DNA in the blood of said patient; such decrease of number average molecular weight might be measured by gel electrophoresis of extracellular blood DNA fraction from the blood of said patient. In one of preferred embodiments the method according the invention can be effectively applied for treatment of diabetes mellitus and atherosclerosis. A DNASE enzyme may be further applied in a dose and regime that results in a DNA hydrolytic activity measured in blood plasma that exceeding 1.5 Kunitz units per 1 ml of blood plasma for more than 12 hours within a period of 24 hours.

The present invention suggests that systemic DNA mutation disease can be treated by reducing of circulating extracellular blood DNA levels.

Development of systemic DNA mutation disease in humans is accompanied by quantitative and/or qualitative change of blood extracellular DNA.

There are no analysis of blood extracellular DNA spectrum and its biological role in systemic DNA mutation disease prior to this invention. A search of the prior art reveals no published data concerning an analysis of blood extracellular DNA spectrum in systemic DNA mutation disease performed by direct cloning and without use of polymerase chain reaction (PCR). PCR can pervert a pattern of blood extracellular DNA because of specificity of primers used for amplification. There is no available knowledge about genetic repertoire of extracellular blood DNA in patients suffering from systemic DNA mutation disease and about biological role of extracellular blood DNA in course of these diseases. Nothing is known about potential therapeutic value of extracellular blood DNA enzymatic destruction for treatment of systemic DNA mutation disease; so, taking into account all aforesaid, the invention complies with requirements of "novelty" criteria (N).

As the applicant established by direct cloning and sequencing of extracellular blood DNA without PCR (Polymerase Chain Reaction), the extracellular blood DNA of patients with systemic DNA mutation disease contains the unique quantitative and qualitative repertoire of genes, which non-randomly represents human genome and contains genetic elements involved in to the development of the disease. It was shown that extracellular blood DNA might promote the development of somatic mosaicism and systemic DNA mutation disease.

It was established that enzymatic destruction of extracellular blood DNA by DNASE enzyme when applied in certain surprisingly high specific doses has significant therapeutic effect on the course of systemic DNA mutation disease.

Aforesaid new characteristics of the claimed invention are based on new ideas about mechanism of development of systemic DNA mutation disease. In this way the claimed method conformances to requirements of "invention step" criteria (IS).

BRIEF DESCRIPTION OF THE DRAWINGS

The advantages and features of the present invention have been explained by detailed description of embodiments with references to drawings.

DESCRIPTION OF THE PREFERRED EMBODIMENTS

Figure 1:
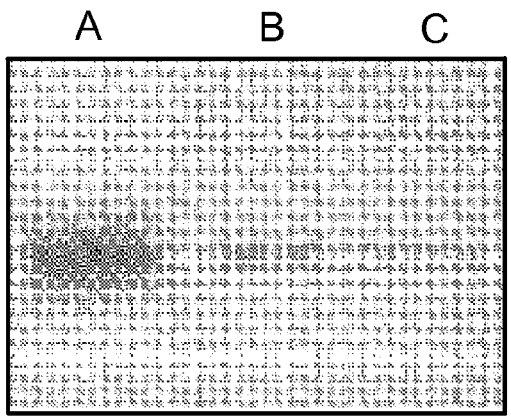
FIG. 1: NF-kappa B expression in (A) cultured aortic endothelial cells treated with extracellular blood DNA fraction from patient suffering from systemic atherosclerosis; (B) cultured aortic endothelial cells treated with extracellular blood DNA fraction from patient suffering from systemic atherosclerosis plus 1 mkg/ml of DNASE1; and (C) control cells.

The inventive method is realized as follows:
Materials and Methods:
The following agents, which destroy extracellular blood DNA, were used: bovine pancreatic DNASE (Sigma, specific activity 2 400 Kunitz units/mg; Samson-Med, specific activity 1 500 Kunitz units/mg), recombinant human DNASE 1 (Gentech, specific activity 1000 U/mg).

Extracellular DNA from blood plasma was isolated as follows: fresh plasma (no more than 3-4 hours after sampling) with anticoagulant (sodium citrate) was centrifuged on Ficoll-Plaque Plus (Amersham-Pharmacia) during 20 minutes at 1500 g. at room temperature. ½ of plasma was detached, not affecting the rest of cells on the Ficoll pillow, and further centrifuged at 10000 g. during 30 min for separation from cell fragments and debris. Supernatant was detached, without affecting of the sediment, and was toped up to 1% of sarkosil, 50 mM tris-HCl, pH 7.6, 20 mM EDTA, 400 mM NaCl, and then mixed with equal volume of phenol-chloroform (1:1) mixture. The prepared emulsion was incubated during 2 hours at t=65° C., then phenol-chloroform mixture was separated by centrifuging (500 g during 20 minutes, room temperature). The procedure of deproteinization with phenol-chlorophorm mixture was repeated 3 times, and then the water phase was processed with chloroform and diethyl ether. Separation from organic solvents was made by centrifugation at 5000 g during 15 minutes. Then equal volume of izopropanol was added to resulting aqueous phase and the mixture was incubated overnight at 0° C. After sedimentation the nucleic acids were separated by centrifugation at 10000 g during 30 minutes. The sediment of nucleic acids was dissolved in of 10 mM tris-HCl buffer, pH 7.6 with 5 mM EDTA, and inflicted to the CsCl gradient (1M, 2.5M, 5.7M) in test-tube for rotor SW60Ti. The volume of DNA solution was 2 ml, volume of each step of CsCl was 1 ml. Ultracentrifugation was conducted in L80-80 (Beckman) centrifuge during 3 hours at 250000 g. DNA was collected from the surface of each gradient step into fractions. These fractions were dialyzed during 12 hours (t=4° C.) and pooled. Presence of DNA in fractions was determined by agar electrophoresis and DNA was visualized by ethidium bromide staining. The amount of DNA was determined with spectrophotometer (Beckman DU70) in cuvetts (100 mkl) at wavelength of 220-230 nm.

NOD mice were obtained from <<Pushcino>> animal breeding house.

Example 1

DNASE Treatment Suppresses the Development of Somatic Mosaicism

Frequency of HPRT gene's mutations in blood T-lymphocytes was studied as the model of development of somatic mosaicism in vivo. The human HPRT gene, mapped to chromosome Xq26, codes for a constitutively expressed, but non-essential, enzyme involved in purine metabolism. Mutant peripheral blood T-lymphocytes which do not express a functional HPRT gene product can be enumerated and clonally expanded by selective growth in the normally toxic purine analog 6-thioguanine in the presence of specific mitogens and growth factors. In normal, unexposed individuals the frequency of 6-thioguanine resistant T-lymphocytes is typically $10^{-6}$ to $10^{-5}$ (R. J. Albertini, J. A. Nicklas, J. P. O'Neill, S. H. Robison, In vivo somatic mutations in humans: measurement and analysis, Annu. Rev. Genet. 24 1990. 305-326.) Molecular analyses of the mutant, HPRT deficient, clones have demonstrated that 85% of the gene inactivating mutations observed in unexposed adults arises by localized HPRT gene alterations—single base changes, small deletions or insertions and frame shift.

Selective lymphocyte cloning was performed using peripheral blood of 8 female patients with different forms of advanced cancer who got surgical resection at Kostushko municipal Hospital (St. Petersburg) and immunomodulation therapy at neoadjuvant setting (Neovir, 250 mg IM once every 2 days for 3 weeks). Following surgical resection 4 patients were further treated by IV infusions of bovine pancreatic DNASE (Samson) according the following schedule: 2000 mkg/kg×4 times daily for 21 day. Following completion of treatment the patients were assayed for HPRT (−) mutation in blood lymphocytes.

Mononuclear cells were isolated from the whole blood samples using Ficoll-Paquee (Becton Dickinson). Mitogenic stimulation of the separated lymphocytes ($1\times10^6$/ml) was initiated with 1 mg/ml phytohemagglutinin (PHA) in RPMI 1640 media supplemented with penicillin (100 U/ml), streptomycin (100 mg/ml), 20% nutrient medium HL-1 and 5% BSA at 5% $CO_2$ at 37° C. for 24 h. Following wash the cells were then seeded in 96-well round-bottomed plates at cell density of $2\times10^4$ cells per well in selection medium to determine cloning efficiency. The cells were plated in 200 ml of the RPMI medium containing 1 mg/ml 6-thioguanine, 0.125 mg/ml PHA, 20% HL-1 and 5% BSA supplemented with interleukin-2 (BD Biosciences, 10 BRMP units/mi). Four 96-well plates were seeded for each patient. After 5 days of culture, the colonies on mutant selection plates were scored for growth using an inverted microscope.

The results of selective T-lymphocyte cloning are presented in the table below:

| Patient | Treatment | Total number of wells | HPRT wells (growth positive) |
| --- | --- | --- | --- |
| KNP | DNASE | 384 | 7 |
| PGP | DNASE | 384 | 12 |
| BAI | DNASE | 384 | 2 |
| FVV | DNASE | 384 | 11 |
| SLS | NO | 384 | 47 |
| GAN | NO | 384 | 22 |
| PMI | NO | 384 | 31 |
| ENV | NO | 384 | 55 |

Thus, inventive treatment suppresses spread of HPRT (−) mutation and suppresses the development of somatic mosaicism.

Example 2

Extracellular Blood DNA Promotes the Development of Somatic Mosaicism

The extracellular blood plasma DNA was purified from blood of patient ENV as specified in methods section. Mononuclear cells were isolated from the whole blood samples of patients KNP, PGP, BAI and FW as specified in Example 1. The mitogenic stimulation and selective cloning were performed as specified in Example 1 with modification as follows: during mitogenic activation stage lymphocyte cultures of patients KNP, PGP, BAI and FW were supplemented with 50 mkg/ml of extracellular blood plasma DNA purified from patient ENV. After 5 days of culture, the colonies on mutant selection plates were scored for growth using an inverted microscope. The results of selective T-lymphocyte cloning are presented in the table below:

| Patient | Total number of wells | HPRT wells (growth positive) |
|---------|----------------------|------------------------------|
| KNP | 384 | 18 |
| PGP | 384 | 15 |
| BAI | 384 | 21 |
| FVV | 384 | 31 |

Thus, extracellular blood DNA promotes the development of somatic mosaicism.

Example 3

Sequencing of Extracellular Blood DNA from the Patient Suffering from Type 2 Diabetes and Systemic Atherosclerosis Treatment of Atherosclerosis A 54-year-old man has been admitted to the Cardiothoracic surgery department of Kostushko municipal hospital (St. Petersburg) in severe condition complaining on intensive pain in abdomen, diarrhea, intensive pain in legs that appear during walking, loss of weight. Diabetes mellitus type 2 was diagnosed 12 years ago and glybencamide was prescribed. Pain in epigastrium after food intake appeared 15 months ago. Antacids were prescribed but pain continued to increase and steatorrhea appeared in the last 3 months. Because of intensive pain syndrome anorexia has developed in a couple of days prior admittance. Considerable exhaustion (body weight was 44 kg; body weight loss was 28 kg for the last 5 months) and absence of arterial pulsation on legs were found out during examination. No organic changes were observed during gastroduodenoscopy and colonoscopy. Electrocardiographic data was not changed pathologically. Moderate increase of cholesterol level and low-density lipoprotein fraction was observed in blood analysis. Glycated hemoglobin' level was 11%. Partial occlusion of aorta below renal artery (70%), partial occlusion of iliac arteries (90%), total occlusion of upper and lower mesenteric artery were observed on aortography.

The probes of patient's extracellular blood DNA were taken before initiation and on day 35 of therapy. The extracellular DNA was cloned by the method which allows to get non amplified plasmid libraries of blood extracellular DNA with representativeness up to one million of clones with the average size of 300-500 base pairs. The DNA which has been isolated using the protocol specified in Materials and Methods section was treated with Proteinase K (Sigma) at 65° C. and subjected to additional phenol-chloroform extraction step with further overnight precipitation by ethanol. The DNA fraction was than treated by Eco RI restrictase or by Pfu polymerase (Stratagene) in presence of 300 mkM of all desoxynucleotidetriphosphates for sticky-ends elimination. The completed DNA was phosphorylated by polynucleotidkinase T4 and ligated to pBluescript plasmid (Stratagene), which had been digested with EcoRI or Pvull and dephosphorylated by phosphatase CIP (Fermentas). The process of ligation was conducted with Rapid Legation Kit (Roche). The ligated library was transformed into DH12S cells (Life Technologies) by electroporation (*E. Coli* porator; BioRad). 12-20 electroporation covets were used for the transformation of one library. The library serial dilutions were cloned on 1.5% agar and LB media supplemented with ampicillin. In both cases the libraries represented 2-3×10$^6$ clones.

Analysis of 75 randomly selected clones with the size 300-1000 base pairs from the "before treatment" library revealed 56 clones containing unique human DNA sequences as presented at the table below:

| Gene | Number of clones | Potential role in Atherosclerosis/diabetes mellitus |
|------|------------------|------------------------------------------------------|
| Neutral endopeptidase | 2 | At atherosclerosis its activity is increased in endothelial cells, nonstriated muscle cells, stromal cells of artery' intima. Decreasing of its activity can decrease lipids accumulation in vessels wall. |
| Muskelin 1 | 1 | Works as mediator of cell response on thrombospondin 1. Thrombospondin 1-mediated processes are pathophysiological components of atherosclerotic affection of artery wall. |
| Nf-kappaB | 3 | At hyperglycemia and atherosclerosis activity is increased in cells of artery wall. |
| E-selectin | 3 | High level of expression is a risk factor of angiopathy development at diabetes type 2. |
| GAD2: glutamate 2 decarboxylase 2 | 2 | One of the main pancreatic autoantigens. |
| Phospholipase C, epsilon | 2 | Induces expression of receptors of low-density lipoproteins |
| BAI3: brain-specific angiogenesis inhibitor | 1 | Angiogenesis inhibitor |
| Nicotinamide nucleotide transhydrogenase | 1 | Involved in detoxification of reactive oxygen species and insulin secretion. |
| 17 kD fetal brain protein | 1 | UNCLEAR |
| CRTL1: cartilage linking protein 1 | 1 | Involved in morphogenetic process in heart and large vessels |
| Transient receptor potential cation channel | 1 | UNCLEAR |

Thus, extracellular blood DNA from patient having diabetes mellitus and systemic atherosclerosis contains significant non-random presence of human disease-relevant unique genomic DNA.

Patient was considered as not eligible for surgery so, conservative therapy was chosen. Intensive IV nutrition was started. Insulin and anti-aggregation therapy have being started. Under patient consent daily intravenous infusions of bovine pancreatic DNASE (Samson) at daily dose of 800 mg (1 200 000 Kuntz units) divided to 4 two-hour deliveries were started. Week after start of DNASE therapy pain syndrome disappeared and patient was allowed to take light dietetic food orally. 20 days after start of DNASE treatment patient was switched to full value oral nutrition. General state was improved, body weight has increased. 45 days following initiation of DNASE treatment patient was reexamined by angiography. 20% decrease of aorta occlusion and 35% decrease of iliac artery occlusion level as well as appearance of blood circulation in upper and lower mesenteric was observed. Patient was considered as eligible for revascularization surgery.

Extracellular blood plasma DNA sampled from patients blood at day 35 following start of DNASE therapy was assayed by gel electrophoresis and cloning. Analysis of 50 clones randomly chosen from the library obtained from the extracellular blood plasma DNA of patient on the day 35 after the beginning of treatment has shown that more than 90% of revealed clone sequences are short fragments of repetitive human DNA with the dominance of alpha-satellite DNA.

Example 4

Influence of Extracellular Blood DNA from the Patient with Systemic Atherosclerosis on Disease Causing Protein Expression in Aortic Endothelial Cells Endothelial NF-kappa B signaling orchestrates proinflammatory gene expression at the arterial wall and promotes the pathogenesis of atherosclerosis. Here we assayed the influence of extracellular blood DNA from the patient diagnosed with systemic atherosclerosis on NF kappa B expression in primary aorta endothelial cell culture. Blood plasma was obtained from vascular surgery clinic of St. Petersburg Medical Academy from the patient undergoing femoro-femoral bypass surgery due to severe atherosclerotic arterial occlusion.

The extracellular blood DNA was purified as described in Materials and Methods section. The aortic endothelial cells (C-006-5C; Invitogen) were plated at density of $5-8\times10^2$ cells/mm$^2$ in multiwell (12×) cell culture plates in Clonetics® EGM®-2MV media (Lonza Cologne AG) and incubated for 48 h. at 37° C. and 5% $CO_2$. Following 24 h of growth the culture media was supplemented with 50 mkg/ml of patient extracellular blood DNA fraction or 50 mkg/ml of patient extracellular blood DNA fraction plus human recombinant DNASE-1 (Genentech) at 1 mkg/ml concentration.

After 24 h. culturing the explants were lysed in buffer containing 20 mM Tris-HCl, 150 mM NaCl, 1 mM phenylmethylsulfonylfluoride, 5 mg/ml aprotinin, 0.5% Nonidet P-40 (Sigma-Aldrich) for 1 hour at 4° C. The lysates were centrifuged for 10 min at 20,000 rpm. The supernatants were diluted with reducing sample buffer and were separated by electrophoresis on a 10% SDS-PAGE gel (20 mkg protein per lane loaded). The proteins were transferred onto Hybond-C-nitrocellulose membrane (Amersham Italia, Milan, Italy. For immunoblot analysis, the membranes were incubated with the NF-.kappa.B antibodies (Stressgen). The bands were detected using the chemiluminescence system.

The results are presented at the FIG. 1. Extracellular blood DNA fraction from patient suffering from systemic atherosclerosis increases the expression of NF-kappa B in cultured aortic endothelial cells and treatment with DNASE ameliorate this effect.

Example 5

Treatment of Diabetes Mellitus

Figure 2A:
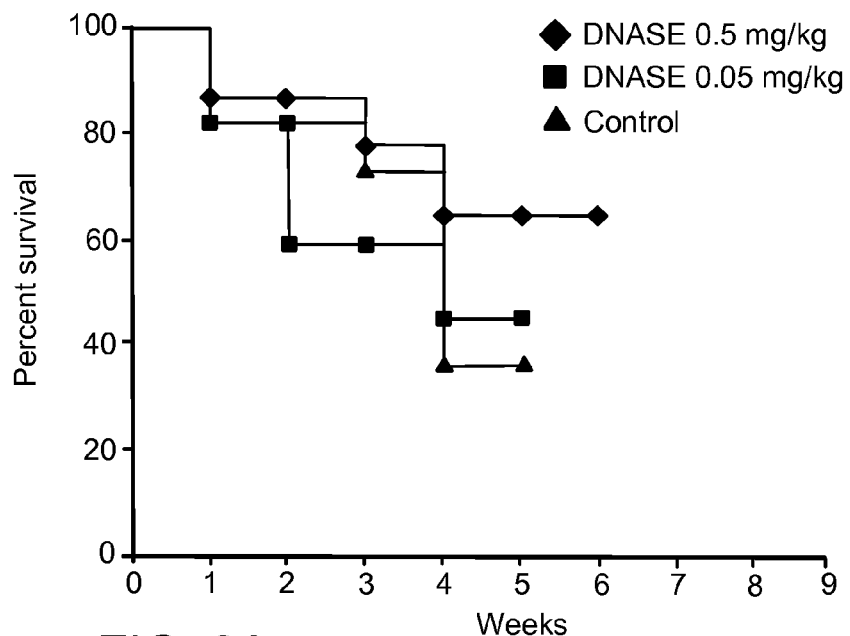
FIG. 2: Panel A shows a graph of the survival of NOD diabetic mice treated with different doses of DNASE1—50 mkg/kg, 500 mkg/kg, and control; Panel B shows average molecular weight of extracellular blood plasma DNA (as measured by electrophoresis) in blood of NOD diabetic mice treated with 50 mkg/kg DNASE 1 (A), 500 mkg/kg DNASE1 (B), and control (C).
Figure 2B:
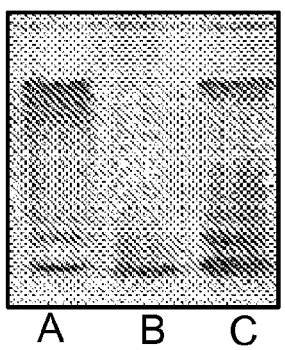

Non-obese diabetic (NOD) mice exhibit a susceptibility to spontaneous development of autoimmune insulin dependent diabetes mellitus. 60 NOD mice were recruited to the study at the age of 14 weeks when all of them became hyperglycemic. The recombinant human DNASE 1 (Gentech) at 50 mkg/kg and 500 mkg/kg was administered intramuscularly twice daily for 21 day. 2 mice from each group were sacrificed at the last treatment day to perform evaluation of extracellular blood plasma DNA. The efficacies of DNASE were assessed based on the survival rate at day 35. The results of experiments are presented at the FIG. 2. There is evident increase in survival of mice treated with 500 mkg/kg DNASE 1; such survival is accompanied with decrease of average molecular weight of extracellular blood plasma DNA (as measured by electrophoresis) in blood of NOD diabetic mice. Thus, high doses of DNASE according to inventive treatment are able to decrease the quantities of circulating extracellular blood plasma DNA and are effective against systemic DNA mutation disease-diabetes mellitus.

Example 6

Treatment of Diabetes Mellitus

A 46-years-old patient with 3 years history of type 2 diabetes mellitus was admitted to the internal therapy clinic of St. Petersburg Medical Academy. Patient failed to achieve proper glucose control using oral hypoglycemic agents including those of thiazolidinediones, biguanides and sulfonylureas. Patient was switched to 0.3 IU/kg of NPH insulin monotherapy (21 IU daily) and discharged from clinics under the supervision of ambulatory endocrinologist. Three month later patient was readmitted to the clinic since glycosylated hemoglobin (HbA1) level was still too high (above 10%) with evolving microalbuminuria and decrease in vision sharpness despite daily insulin dose was adjusted up to 1.2 U/kg (84 U/day) during ambulatory period. Under patient consent he was assigned for intramuscular injections of bovine pancreatic DNASE (Samson) twice daily at 200 mg/day dose for 4 months and again discharged from clinics. At 4 month after initiation of treatment patient were reexamined in clinics outpatient department. Significant improvement in insulin sensitivity, improvement of glycemia control and normalization of kidney function has been reported by patient ambulatory endocrinologist and confirmed by laboratory examination in clinic. The effect of DNASE treatment on patient disease indicators is presented in table below:

| Indicator | Prior DNASE treatment | At DNASE course completion |
|---|---|---|
| Insulin requirement | 1.2 IU/kg | 0.6 IU/kg |
| HbA1 | 13.2% | 7.2% |
| 24 h. albuminuria | 275 mg | 60 mg |

Thus, the inventive treatment is effective in diabetes mellitus.

Example 7

Atherosclerosis is a systemic disease that is accompanied by formation of specific atherosclerotic plaques in large and middle sized artery walls. Depends on the localization, stage and size of atherosclerotic plaques the disease has different clinical signs (angina, stroke and so on). The signs especially associated with organ dysfunction caused by systemic atherosclerosis are cured by drug therapy or by surgical operation. There is no cure for Atherosclerosis by drug therapy methods as for any systemic disease. An established method of prevention that delays the disease progression is therapy with inhibitors of 3 3-hydroxy-3-methylglutaryl-CoA (HMG CoA) reductase (Lovastatin, Parvastatine e.t.c.) leading to the inhibition of endogenous cholesterol synthesis and increasing of clearance of low density lipoproteins of blood plasma and it attenuates atherosclerosis development (New Concepts and Paradigms in Cardiovascular Medicine: The Noninvasive Management of Coronary Artery Disease, K. Lance Gould, THE AMERICAN JOURNAL OF MEDICINE, Volume 104, Jun. 22, 1998, 2s-17s). Disadvantages of such treatment are adverse effects (A safety look at currently available statins, Moghadasian M H, Expert Opin Drug Saf 2002 Sep. 1 pp. 269-74) and limited efficacy (Statins: balancing benefits, efficacy and safety, Clearfield M B, Expert Opin Pharmacother, 2002, May 3 pp. 469-77).

Influence of DNase Therapy on the Viability of Pancreatic Beta-Cells and Endothelium of Aorta Human recombinant DNase I (Gentech) was used. β cells of human embryonic pancreas and endothelial cells of human aorta were used for primary cell culture formation. DNA isolated from plasma of patient with severe form of diabetes mellitus type 2 that was complicated by atherosclerosis (0.0025 mkg on 1 ml of culture media) was added to one of the experimental series in cell culture 24 hours after passage and DNA extracted from the blood of the same patient but treated by DNase (1 mkg/ml; 37 C; 30 minutes) was added to the second series of cell culture. The number of viable cells was counted using the trypan blue uptake technique in a 24 hours.

Results of the experiment are presented in table 4:

TABLE 4

Percentage of viable cells 48 hours after their cultivation (in percents).

| Cells | Control | DNA of patient | DNA of patent treated by DNse |
|---|---|---|---|
| β cells | 73% | 43% | 61% |
| Endotelium | 62% | 35% | 55% |

Thus extracellular blood plasma DNA of patient with severe form of diabetes mellitus type 2 and atherosclerosis negatively influence both the normal pancreatic β-cells and the normal endothelial cells. Destruction of the patient' blood extracellular DNA prevents development of negative influence according to the claimed method.

Example 8

Isolation of Free Circulating DNA from Blood Plasma

Fresh blood plasma (not more than 3-4 hours after isolation) with anticoagulant (sodium citrate) addition was centrifuged on Ficoll-PlaquePlus (Amersham-Pharmacia) step at 1500 g for 20 minutes at room temperature. Plasma (½ of all amount) was neatly isolated avoiding touching cells sediment on ficoll step and was centrifuged at 10 000 g for 30 minutes to eliminate cells and debris. Supernatant was taken away not touching sediment and up to 1% of sarcosile, up to 50 mM of tris HCl pH 7.6, up to 20 mM EDTA, up to 400 mM NaCl and equal volume of phenolchloroform mixture 1:1 were added. Received emulsion was incubated at 65° C. for 2 hours than phenol-chloroform was separated by centrifuging at 5000 g during 20 minutes at room temperature. Deproteinization by phenol-chloroform method was identically repeated for three times after what water phase was processed by chloroform and after it by diethyl ether.

Organic solvents' separation was done by centrifuging at 5000 g during 15 minutes. Equal part of isopropanol was added to water phase and incubated during night at 0° C.

After sedimentation nucleic acids were separated by centrifuging at 10 000 g during 30 minutes. Sediment of nucleic acids was dissolved in buffer that consisted of 10 mM tris-HCl, pH 7.6, 5 mM EDT A and was inflicted on step made from chlorine cesium gradient (1M, 2.5M 5.7) in centrifuge test tube for SW60Ti rotor. DNA volume was 2 ml, volume of each CsCl step was 1 ml. Ultracentrifuging was done in L80-80 (Beckman) centrifuge for 3 hours at 250000 g. DNA was isolated according to fractions from the step's surface 5.7M. Fractions were dialized during 12 hours. mM tris-HCl, pH 7.6, 1 mM EDTA at 4° C. will be added. DNA presence in fractions was defined by agarose electrophoresis with DNA visualization by ethidium bromide. DNA amount was spectrophotometric ally estimated (Beckman DU 470) in cuvette with volume 100 mkl, using 220-320 nm spectrum. Average runout of DNA was 10-20 ng according to 1 ml of plasma.

Cloning and Sequencing of Blood Plasma DNA.

We have developed new method of DNA isolation and cloning from blood plasma, that allows to construct not amplified plasmide library of such DNA with representativeness up to million clones with average size 300-500 base pair isolated from 50 ml of blood, even taking into account significant amount of elevated liposaccharides level and non identified mixtures that troubled purification of nucleic acids. So representative analysis can be done with less amount of plasma pattern-10-20 ml depending on pathological contaminates' presence.

Isolated according to above-mentioned method DNA was deproteinized with the use of proteinase K (Sigma) at 65° C. for tightly-bound proteins elimination. After deproteinization DNA was processed by phenol-chloroform at 65° C. and sedimented by 2.5 volumes of ethanol during night. After it DNA was processed by EcoRI restrictase during 3 hours or by Pfu polymerase (Stratagene) at the presence of 300 mkM of all desoxynucleothydethreephosphates for "sticky" edges elimination. Completed DNA was phosphorylated by polynucleotide kinase T4 (30 U, 2 hours). Received samples/preparations were ligated in Bluescript (Stratagene), plasmid digested by EcoR1 or PvuII accordingly and dephosphorylated by alkaline phosphatase CIP (Fermentas) during 1 hour. 1 mkg of vector and 0.1-0.5 mkg of serum DNA were usually used for ligation. Ligation was done by Rapid Ligation Kit (Roche) use for 10 hours at 16° C. Volume of ligase mixture was 50 mkl. Ligated library was transformed into DH12S (Life Technologies) cells with electroporator (BioRad) use. For transformation of one library 12-20 electroporation cuvettes were used. Dilutions of the library at concentrations $10^{-4}$, $10^{-5}$ and $10^{-6}$ were plated for control on dishes with 1.5% agar and LB media, supplemented with 100 mkg\ml ampicillin. In both cases library's representativeness was approximately $2-3 \times 10^6$ clones.

Theoretically set of DNA sequences that circulate in plasma should correspond to set of genome's DNA sequences. Usually cells apoptosis is accompanied by quantitative and nonspecific DNA degradation before its exit out of the cell, so the most wide spread DNA in plasma should be repetitive elements of genome in proportion that correspond to nonspecific degradation of DNA.

Such elements are L1 repeats, satellite DNA, Alu, MER, MIR, THE repeats and some others. Quantity of unique sequences should be small in accordance to their small percent in human genome they may be not detected in cloning DNA without PCR.

Blood plasma DNA library of oncological patient with clinically advanced tumor stage.

We have constructed blood plasma DNA library of patient with diagnosed advanced stage mesothelioma. Representativeness of library was $8.5 \times 10^5$ clones, that is a good result, taking into account rather small amount of DNA (5 μg) received after purification from non character for healthy donors liposaccharides that were in extremely high concentrations at plasma of patient.

We have got the unexpected results after analysis of 96 clones with length from 300 up to 1000 base pairs. (It is necessary to mention that only one clone was not identified as human DNA. For all others correspondent information from HumanGenBank that identifies DNA of these clones as human DNA was received.) As mentioned above, according to data from literature it is logically to assume that there will be a lot of highly repetitive elements in DNA samples.

But at least 55 out of 96 clones presented unique sequences of human DNA. Taking into account real ratio of repetitive and unique elements of human genome (95% to 5%) it is obvious that blood plasma DNA repertoire of this patient differs a lot from human genomic DNA repertoire. In this sample an abrupt enrichment by unique DNA sequences is observed.

For 15 out of 55 unique DNA fragments that were identified during sequencing of 96 clones from the library of blood plasma DNA, functions or product of correspondent gene were identified. Tables 1-15 present list of these sequences and information about their participation in formation and maintenance of "malignant phenotype".

TABLE 1

| Clone | Product | Participation in oncogensis | Source |
|---|---|---|---|
| Clone 24 | Member of G protein - coupled receptor family | Playing major role in cancer cell signalling. Linked with cell transformation, supression of apoptosis, hormone independence and metastasis | Steeg P. S., Nat Rew Cancer, 2003, v. 3, pp. 55-63. Raj G. V, J Urology, 2002, v. 167, pp. 1458-1463. Hoff A. O., Neoplasia, 1999 v. 1, pp. 485-491. |

TABLE 2

| Clone | Product | Participation in oncogensis | Source |
|---|---|---|---|
| Clone 43 | Snf2-coupled CBP activator protein (SCRAP) | Transcription activator. Family members linked with synovial sarcoma and leukaemia development | Thaete c., Hum Mol Genet, 1999, v. 8, pp. 585-91. Monroy M, A., J Biol Chem,. 2001, v. 27 6, pp. 40721-40726 Lee D. W., Cancer Res., 2000, v. 60, pp. 3612-3622. |

TABLE 3

| Clone | Product | Participation in oncogensis | Source |
|---|---|---|---|
| Clone 51 | SRY-box containing gene | Transcription modulator. Expressed during embryogenesis. Family members linked with medulloblastomas, gonadal tumors, highly metastatic melanoma. | Graham J. D., J Mol endocrinol, 1999, v. 22, pp. 295-304. Lee C. J., J Neurooncol, 2002, v. 57, pp. 201-214. Uehara S., Cancer Genet Cytogenet, 1999, v. 113., pp. 78-84. Tani M., Genomics, 1997, v. 39, pp. 30-37 |

TABLE 4

| Clone | Product | Participation in oncogensis | Source |
|---|---|---|---|
| Clone 72 | Protein-tyrosine kinase | Family members playing major role in cancer. Some PTK are cellular specific oncogenes products. | Hunter T., Philos Trans R Soc Lond B Biol Sci, 1998, v. 353., pp. 583-605. Scheijen B., Oncogene, 2002, v. 21., pp. 3314-3333. |

TABLE 5

| Clone | Product | Participation in oncogensis | Source |
|---|---|---|---|
| Clone 83 | Fibroblast activation protein alpha; cell surface serine protease | Family members playing role in cancer invasion and metastasis. The product is active in cancer stroma and different carcinomas. | Chen W. T, Enzyme Protein, 1996, v. 49., pp. 59-71. Scanlan M. J., Proc Nat Acad Sci USA, 1994, v. 91, pp. 5657-5661. Mathew S., Genomics, 1995, v. 25, pp. 335-337. |

TABLE 6

| Clone | Product | Participation in oncogensis | Source |
|---|---|---|---|
| Clone 86 | Brain testican | Proteoglycan with unknown function. Linked with neoplastic phenotype of embryonal rhabdomyosarcoma cells. | Genini M., Int J Cancer, 1996, v. 66, pp. 571-577. |

TABLE 7

| Clone | Product | Participation in oncogensis | Source |
|---|---|---|---|
| Clone 152 | KRAB domain, Zn-finger proteins | Family members are known as transcription repressors. Linked with early embryogenesis, neuroblastoma, Ewing sarcoma, Tcell lymphoma, in progression and chemoresistance in lung cancer. | Oguri T., Gene, 1998, v. 222, pp. 61-67 Gou D. M., Biochim Biophys Acta, 2001, v. 1518, pp. 306-310 Margolin J. F., Proc Nat Acad Sci USA, 1994, v/91, pp. 4509-4513. Bellefroid E. J., EMBO J, 1993, v. 12, pp. 1363-1374 Gonzales-Lamuno D., Pediatr Pathol Mol Med, 2002, v. 21, pp. 531-540. |

TABLE 7-continued

| Clone | Product | Participation in oncogensis | Source |
|---|---|---|---|
| | | | Marilee J. W., Gene, 1994, v. 152, pp. 227-232. |

TABLE 8

| Clone | Product | Participation in oncogensis | Source |
|---|---|---|---|
| Clone 190 | Antigen linked with melanoma | Antigen recognized by autologous tumor infiltrating lymphocytes. | J. Immunol. 166(4), 2871-2877, 2001 |

TABLE 9

| Clone | Product | Participation in oncogensis | Source |
|---|---|---|---|
| Clone 167 | N-cadherin | Cell adhesion molecule with major role in cancer growth, invasion and metastasis. | Hazan R. B., J Cell Biol, 2000, v. 148, pp. 779-790. Li G., Cancer Res, 2001, v. 61, pp. 3819-3825. Tran N. L, J Biol Chern, 2002, v. 277, pp. 32905-32914. |

TABLE 10

| Clone | Product | Participation in oncogensis | Source |
|---|---|---|---|
| Clone 197 | FAFI: Fas associated factor 1 | Phosphoprotein known to be the proapoptosis factor. | Jensen H. H., Int J Biochem Cell Biol, 2001, v. 33, pp. 577-589. Ryu S. W., Biochem Biophys Res Commun, |

TABLE 11

| Clone | Product | Participation in oncogensis | Source |
|---|---|---|---|
| Clone 114 | Interleukin 7 | Proposed as essential paracrineautocrine growth factor for variety of cancers. | Trinder P., Int J Oneol, 1999, v. 14, pp. 23-31. Cosenza L., Cell Signalling, 2002, v. 14, pp. 317-325. |

TABLE 12

| Clone | Product | Participation in oncogensis | Source |
|---|---|---|---|
| Clone 208 | DEAD Box RNA helicase-like protein | Family members involved to RNA methabolism. Linked to exponential cell growth in cancer. | Iggo R. D., Mol Cell Biol, 1991, v. 11, pp. 1326-1333. Causevic M., Oncogene, 2001, v. 20, pp. 7734-7743. |

TABLE 13

| Clone | Product | Participation in oncogensis | Source |
|---|---|---|---|
| Clone 97 | Lipin 1 | One of tumor cells' response regulators on cytotoxic compounds. | Brachat A. et. al., Oncogene, 2002, v. 21, pp. 8361-8371 |

TABLE 14

| Clone | Product | Participation in oncogensis | Source |
|---|---|---|---|
| Clone 121 | Dynein | Takes part in transport of p53 protein, is hypersecreted at cancer of prostate and hepatocellular cancer. | Bull J. H., et. al., Br J Cancer, 2001, v. 84, pp. 1512-1519. Giannakakou P., et. al., Nat Cell Biol, 2000, v. 2, pp. 709-717 Jiang 1, et. al., Gene, 2001, v. 281, pp. 103-113. |

TABLE 15

| Clone | Product | Participation in oncogensis | Source |
|---|---|---|---|
| Clone 178 | Ramp protein | Linked with human embrional carcinoma cells' development. | Cheung W. M., et. al., J Biol Chern, 2001, v. 276, pp. 17083-17091 |

In this way 14 out of 15 sequences with identified function or protein that encodes different products (protein kinases, growth factors, proteinases, adhesive molecules and regulatory nuclear proteins) are described in literature as related to "malignant phenotype" formation and maintenance. Only product of $197^{th}$ clone identified as pro-apop-totic factor is not clearly linked with malignant progression. Though there is data concerning relationship between high apoptotic activity of tumor with its progression (Nishimura R., et al., J Surg Oncol, 1999, v. 71, pp. 226-234) and possible role of apoptotic inductors in formation and maintenance of immunosupression in malignant growth (O'Connel J., et al., Dis Esophagus, 1999, v. 12, pp. 83-89).

The most significant presence from repetitive elements in this material was alpha-satellite DNA (30 clones). It is possible to say that that alpha-satellite DNA was the only highly repeated element from human genome, which behaves exactly as repeat in this material. The rest of highly repetitive elements were presented in material as one or several clones (L1 variant and MLT26), or were not found among patterns (MER, Alu, THE, MIR, β-satellite). Based on today's knowledge one can assume that plasma blood composition for the most part should repeat composition of genome DNA, so listed repeats should be represented in the major part of clones while unique and moderately repeated consequences in analysis of such a small number of clones should not be recognized at all. Received result clearly indicates on special way of plasma DNA formation in oncological patients. Another unexpected result is that of finding in the material of two new moderately repeated sequences—duplicones, that were recently unknown, also support the evidence of special way of plasma DNA formation in patients with malignant tumor. For the first time duplicones were found in human genome less then two years ago. Known duplicones (Eichler E. E., et al., Genome Res, 1998, v 8, pp. 791-808; Ji Y, et al., Genome Res, 2000, v. 10, pp. 597-610; Pujana M. A., et al., Genome Res, 2001, v. 11, pp. 98-111) are extensive regions of DNA that were multiplied for several times in the frame of one chromosome (unlike other repeats that are randomly allocated in genome). Duplicones' formation and expansion is connected with different genetic syndromes (for example Prader-Willi/Angelmane syndrome), with multigenic families' evolution such as MHS (Shiina T., et al., Proc Nat Acad Sci USA, 1999, v. 96, pp. 13282-13287) and with chromosome instability in tumors.

It is necessary to mention that analysis of clones received from blood plasma DNA of patient has given us unexpected results.

Blood plasma DNA of oncological patient is highly enriched with unique genes. 55 out of 96 analyzed clones contain fragments of genome's unique sequences. 14 out of 15 sequences with identified in functions refer to process of tumor progression and maintenance of "malignant phenotype".

Strong impoverishment of the most wide spread human repeat such as MER, Alu, THE, MIR, β-satellites is found in plasma DNA material.

Finding of two consequences with previously unknown duplicones' characteristics indicates on dupli-cones' representativeness in such DNA samples.

DNA Library of Healthy Donor's Blood Plasma.

For method's value proof of blood plasma DNA cloning and sequencing for identification of genome's unique genetic consequences we have constructed DNA library of healthy donor's blood plasma. It is known that plasma of clinically healthy people also contains DNA but in significantly less amount than plasma of oncological patients (Shapiro B., et al., Cancer, 1983, v. 51, pp. 2116-2120).

Representativeness of library was near $8\times10^5$ clones. We have got interesting result after analysis of 70 clones with length from 300 up to 1000 base pairs. We found out that 58 out of 70 analyzed clones are unique DNA sequences of human genome. After searching the HumanGenBank, we identified the function or product of correspondent gene for 14 out of 58 unique DNA fragments.

Only 12 clones contained fragments of repetitive sequences, herewith without of alpha-satellite DNA dominance.

So, it was unexpectedly found out that blood plasma DNA of healthy people and oncological patients for the most part contain unique fragments of human genome. In the case of oncological pathology unique sequences of blood plasma DNA correspond to genes which products take part in the formation and maintenance of tumor cell's "malignant phenotype".

Basing on this unexpected discovery we have suggested that DNA circulating in patient's blood can be messenger of horizontal genetic information transfer during the course of oncological diseases, assisting to accumulation and spreading of genes that are necessary for "malignant phenotype" formation and maintenance within population of tumor cells.

Somatic mosaicism is a condition that is a result of genetically non-identical somatic cells' presence in organism. Modern vision presents that many non tumor and noninfectious (so called somatic) human diseases (for example atherosclerosis, diabetes, nonspecific chronic lung diseases and so on), including aging process, are connected with appearance and spreading (expansion) in the process of individual development of somatic cells' clones that have mutant genes. (Youssoufian H., et al., Nature Rew. Genet., 2002, v. 3, pp. 748-758; J. Vijg, Mutation Res., 2000, v. 447, pp. 117-135; R. Erickson, Mutation Res., 2003, v. 543, pp. 125-136; Andreassi M., Mutation Res., 2003, v. 543, pp. 67-87; Anderson G., et al., Trends in Pharmacological Sci., 2003, v. 24, pp. 71-76).

Bright example of such process is progression of mitochondrial heteroplasmia (expansion of mutant mitochondrial DNA) at different diseases and in the aging process (E. Jazin et al., Proc Nat Acad Sci USA, 1996, v. 93, pp. 12382-12387; Michikawa Y. et al., Science, 1999, v. 286, pp. 774-779; Calloway C. et al., Am J Hum Gen, 2000, v. 66, pp. 1384-1397).

There are two alternative models of somatic mosaicism's appearance. The first is appearance of somatic mosaicism as a result of numerous "de novo" mutations in polyclonal cellular pool. The second model is clonal expansion of mutant cells' clone (Khrapko K., et al., Muation Res., 2003, v. 522, pp. 13-19).

In the process of work above the invention we have found that DNA circulating in the blood of healthy people play significant role in somatic mosaicism's development and its binding, destruction or inactivation inhibits development of somatic mosaicism. Binding, destruction or inactivation of circulating in blood plasma DNA provides treatment effect at diseases which appearance is connected with somatic mosaicism's development.

Examples that are mentioned later indicates role of circulating in blood of oncological patients DNA in the development of tumor's resistance to chemotherapy, development of metastasing process, in sepsis development and in some other pathological conditions. High therapeutic effect of blood plasma DNA's binding, destruction or inactivation is found.

Example 9

DNA Clones' Sequences, Received from Free Circulating Blood Plasma DNA of Patient with Malignant Mesothelioma Clone 1
Duplicon, chromosome 15 and Y
Sequence No 1.
Clone 3
Unique, chromosome 2.
Sequence No 2
Clone 8
MLT2B repeat
Sequence No 3
Clone 9
Centromeric satellite DNA
Sequence No 4

Clone 10
MLT2B repeat
Sequence No 5
Clone 20
LIMC4-like (LINE-element)
Sequence No 6
Clone 15
Alpha-satellite DNA
Sequence No 7
Clones 18, 21
Alpha-satellite DNA
Sequence No 8
Clone 24
Unique, family of G protein-bound proteins, chromosome 6.
Sequence No 9
Clone 25
Unique, chromosome 3.
Sequence No 10
Clone 26
SatB1/Vimentin/nuclear matrix binding DNA
Sequence No 11
Sequence 33
Duplicon specific to the chromosome 10
Sequence No 12
Clone 32
alpha-satellite DNA
Clone 35
LTR repeat
Sequence No 13
Clone 36
Unique, chromosome 18
Sequence No 14
Clone 37
Unique, chromosome 4
Sequence No 15
Clone 41
Sequence No 16
Clone 43
Snf2-related CBP activator protein (SCRAP)
Unique, chromosome 16
Sequence No 17
Clone 45
Unique, chromosome 3
Sequence No 18
Clone 47
Alpha-satellite DNA
Clone 51
SRY-box containing gene.
Sequence No 19
Clone 52
Repeat
Sequence No 20
Clone 53, 55
Alpha-satellite DNA
Sequence No 21
Clone 56
Centromeric repeat
Sequence No 22
Clone 60
Gene repeated on several chromosomes, contains MER5A repeat.
Sequence No 23
Clone 62
Repeat
Sequence No 24
Clone 65
Unique, chromosome 2
Sequence No 25
Clone 71
Unique, chromosome 2
Sequence No 26
Clone 72
Unique, chromosome 8
Sequence No 27
Clone 73
Unique
Sequence No 28
Clone 78
Transposon Tigger fragment
Sequence No 29
Clone 81
Sequence No 30
Repeat (LINE)
Clone 82
Unique, chromosome 1
Sequence No 31
Clone 83
Unique, Fibroblast activation protein alpha; cell surface serine protease
Chromosome 2
Sequence No 32
Clone 79
Alpha-satellite DNA
Clone 86
Unique, gene highly similar to brain testican, chromosome 4.
Sequence No 33
Clone 90
Unique, chromosome X
Sequence No 34
Clone 93
Unique, chromosome 9
Sequence No 35
Clones 89 and 92
Alpha-satellite DNA
Clone 96
Fragment LINE.
Sequence No 36
Clone 97
Chromosome 2 unique, Lipin
Clone 98
Unique, chromosome X
Sequence No 38
Clone 102
Chromosome 17 unique
Sequence No 39
Clone 99
Alpha-satellite DNA
Clone 105
Unique, chromosome 13
Sequence No 40
Clone N106
Chromosome 9 unique
Sequence No 41
Clone 107
Unique, chromosome 8
Sequence No 42
Clone N 111
Unique, chromosome 12
Sequence No 43
Clone N 112
Chromosome 5 unique
Sequence No 44

Clone 114
Chromosome 8 unique; Interleukin 7
Sequence No 45
Clone 116
Chromosome 1 unique
Sequence No 46
Clone 121
Chromosome 5 unique; Dynein
Sequence No 47
Clone 115; 119; 120
Alpha-satellite DNA
Clone 125
Chromosome 9 unique
Sequence No 48
Clone 127
Unique chromosome 20
Sequence No 49
Clone 130
Unique, chromosome is not determined.
Sequence No 50
Clone 124
SatB1/Vimentin/nuclear matrix binding DNA
Clone 133
Alpha-satellite DNA
Clone 137
MLT1A2 repeat
Sequence No 51
Clone 140
Unique, chromosome 2; zinc finger protein, sub-family 1A
Sequence No 52
Clone 141
Chromosome 2 unique
Sequence No 53
Clone 143
Fragment of Alu-repeat
Sequence No 54
Clone 144
Chromosome 2 unique
Sequence No 55
Clone 146
Chromosome 4 unique
Sequence No 56
Clone 139 and 142
Alpha-satellite DNA
Clone 148
Repeat (chromosomes 1, 2 and 4)
Sequence No 57
Clone 152
Unique, chromosome 16; KRAB-Domain, zinc finger protein
Sequence No 58
Clone 154
Chromosome 9 unique
Sequence No 59
Clone 161
Fragment LINE
Sequence No 60
Clone 151
Chromosome 5 unique
Sequence No 61
Clone 150
Chromosome 1 unique
Sequence No 62
Clone 153
Chromosome 11 unique
Sequence No 63
Clone 159
Chromosome 6 unique
Sequence No 64
Clone 163
Alpha satellite DNA
Sequence No 65
Clone 166
Chromosome 12 unique
Sequence No 66
Clone 167
Unique, chromosome 18, CDH2; cadherin 2, type 1, N-cadherin
Sequence No 67
Clones 169, 170
Chromosome 18 unique
Sequence No 68
Clone 178
Unique chromosome 1; RAMP: RA-regulated nuclear matrix-associated protein
Sequence No 69
Sequence No 69
Clone 180
Unique, chromosome 20
Sequence No 70
Clone 181
Unique chromosome 18
Sequence No 71
Clone 185
Alpha-satellite DNA
Sequence No 72
Clone 187
Mer repeat
Sequence No 73
Clone 188
HSATII repeat
Sequence No 74
Clone 189
Chromosome 9 unique
Sequence No 75
Clone 190
Chromosome 1 unique; melanoma antigen recognized by T cells 2
Sequence No 76
Clone 195
Chromosome 10 unique
Sequence No 77
Clone 196
Chromosome X unique
Sequence No 78
Clone 197
Chromosome 1 unique, FAF 1: Fas (TNFRSF6) associated factor 1
Sequence No 79
Clone 200
Chromosome 8 unique
Sequence No 80
Clone 202
Unique chromosome 13
Sequence No 81
Clone 205
Alpha satellite DNA
Sequence No 82
Clone 206
Repeat
Sequence No 83

Clone 208
Unique chromosome 8; Human DEAD box RNA helicase-like protein
Sequence No 84

Example 10

DNA Clones Sequences Received from Free Circulating Blood Plasma DNA of Healthy Donor Clone 1
Chromosome 5 unique
Sequence No 85
Clone 9
Unique chromosome 21
Sequence No 86
Clone 7
Unique chromosome 3
Sequence No 87
Clone 8
Chromosome 4 unique
Sequence No 88
Clone 10
18S RNA gene
Sequence No 89
Clone 11
Alu repeat
Sequence No 90
Clone 13
Unique chromosome 3
Sequence No 91
Clone 15
Unique chromosome 1
Sequence No 92
Clone 16
Unique chromosome 3, neutral endopeptidase
Sequence No 93
Clone 17
Chromosome 8 unique
Sequence No 94
Clone 18
Chromosome 1 unique
Sequence No 95
Clone 21
Unique chromosome 19; Zinc Finger protein
Sequence No 96
Clone 22
Unique chromosome 18
Sequence No 97
Clone 23
Unique chromosome 7, muskelin 1
Sequence No 98
Clone 25
Unique chromosome 11
Sequence No 99
Clone 27
Repeat
Sequence No 100
Clone 29
Unique chromosome 6
Sequence No 101
Clone 30
Unique chromosome 14
Sequence No 102
Clone 31
Unique chromosome 17
Sequence No 103

Clone 32
MER4B repeat
Sequence No 104
Clone 33
Chromosome 1 unique
Sequence 105
Clone 34
Unique chromosome 2
Sequence 106
Clone 35
Repeat
Sequence 107
Clone 36
Chromosome 1 unique
Sequence No 108
Clone 37
HERVH repeat
Sequence No 109
Clone 41
Chromosome X unique
Sequence No 110
Clone 42
Chromosome 6 unique
Sequence No 111
Clone 43
Unique chromosome 22; KREMEN1
Sequence No 112
Clone 44
Unique chromosome 14
Sequence No 113
Clone 45
Unique
Sequence No 114
Clone 46
Chromosome 20 unique
Sequence No 115
Clone 47
Nf-kappaB
Sequence No 116
Clone 38
Unique chromosome 16
Sequence No 117
Clone 48
Chromosome 6 unique
Sequence No 118
Clone 53
Unique
Sequence No 119
Clone 51
Chromosome 5 que
Sequence No 120
Clone 59
Unique chromosome 4, NFKB 1: nuclear factor of kappa light polypeptide gene enhancer
Sequence No 121
Clone 61
Repeat
Sequence No 122
Clone 62
L1 repeat
Sequence No 123
Clone 64
Duplicon chromosome 7
Sequence No 124
Clone 65
Ribosomal DNA
Sequence No 125

Clone 66
Ribosomal DNA
Sequence No 126
Clone 75
Repeat
Sequence No 127
Clone 76
Chromosome 4 unique
Sequence No 128
Clone 83
Chromosome 4 unique
Sequence No 129
Clone 85
Unique chromosome 2; phospholipase C, epsilon
Sequence No 130
Clone 87
L1 PA3 repeat
Sequence No 131
Clone 86
Unique chromosome 5; CRTL 1: cartilage linking protein 1
Sequence No 132
Clone 89
Alu repeat
Sequence No 133
KOH 92
Unique chromosome 6
Sequence No 134
Clone 100
Unique, chromosome 6
Sequence No 135
Clone 105
AluSx repeat
Sequence No 136
Clone 111
Alphoid repetitive DNA
Sequence No 137
Clone 112
Chromosome 9 unique
Sequence No 138
Clone 113
Chromosome 22 unique
Sequence No 139
Clone 114
AluSx repeat
Sequence No 140
Clone 116
Unique chromosome 9; 17 kD fetal brain protein
Sequence No 141
Clone 123
Unique chromosome 5
Sequence No 142
Clone 124
Unique chromosome 13
Sequence No 143
Clone 126
Unique chromosome 8
Sequence No 144
Clone 130
Unique chromosome 1
Sequence No 145
Clone 131
Unique chromosome 4
Sequence No 146
Clone 136
Unique chromosome 8
Sequence No 147
Clone 141
Unique chromosome 2
Sequence No 148
Clone 146
Unique chromosome 16
Sequence No 149
Clone 147
Unique chromosome 5; nicotinamide nucleotide transhydrogenase
Sequence No 150
Clone 149
Unique chromosome 9
Sequence No 151
Clone 151
Unique chromosome 16
Sequence No 152
Clone 152
Unique chromosome 6, BA13: brain-specific angiogenesis inhibitor 3
Sequence No 153
Clone 153
Unique chromosome 9, GAD2: glutamate decarboxylase 2
Sequence No 154
Clone 155
Unique chromosome 9
Sequence No 155

Example 11

Dynamics of P-Glycoprotein Expression in Erlich Carcinoma in Mice that Receive Doxorubicin Therapy and DNase I Effect Treatment by Doxorubicin causes expression of P-glycoprotein in tumor tissue that is one of the main MDR (Multi drug Resistance) phenotype mediators. Immunohistochemical staining of mice's tumor histological cuts are listed below.

Mice were subjected to course of 5 day therapy with Doxorubicin (2 mg/kg intravenously daily) or Doxorubicin+DNase I (0.5 mg/kg four times a day during 5 days)

Treatment has begun on the $3^{rd}$ day after tumor's transplantation. Tissue preparations were executed on the 8th day of tumor's transplantation. Multifocal expression of P-glycoprotein was observed in tumor tissue after 5 days of therapy (FIG. 3).

Figure 3:
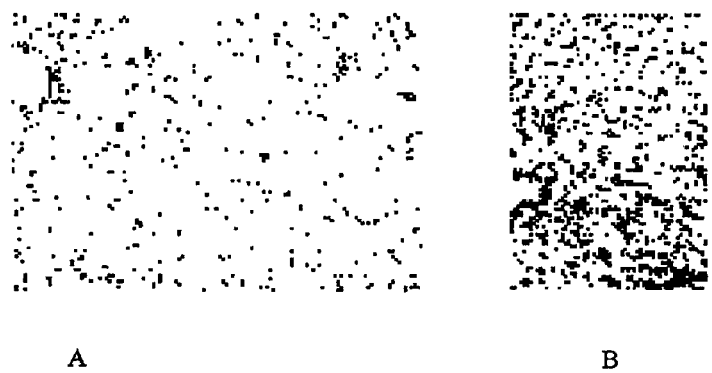
FIG. 3: Results of immunochemical staining of mice tumor's histological slices after administration of 5 day course of Doxorubicin therapy (2 mg/kg every day intravenous) and DNase 1 (0.5 mg/kg four times a day during 5 days). A—Doxorubicin+DNase; B—Doxorubicin.

Total level of P-glycoprotein expression and amount of P-glycoprotein positive nodules in tumor tissue was much lower at the case of combined treatment by Doxorubicin+DNase (FIG. 3). So treatment by DNase delays development of multidrug resistant phenotype in tumor that is caused by antitumor antibiotic Doxorubicin use.

Example 12

Influence of Plasma DNA of C57B1 Mice with LLC Tumor after Chemotherapeutical Treatment by Doxorubicin, on LLC Tumor Growth and Metastasizes Development at C57B1 Mice Receiving Doxorubicin Therapy and Effect of DNase I LLC tumor was replanted to 30 C57B1 mice. Twenty mice were treated with Doxorubicin at 2 mg/kg dose daily for 5 days, starting day 3 after transplantation. Ten mice were treated with Cyclophosphamide at 15 mg/kg dose intraperitoneally for once on the $3^{rd}$ day after replantation. Such treatment scheme does not lead to animal's recovery but leads to 50% tumor inhibition at day 8 in doxorubicin treated animals and 30% tumor inhibition at day 8 in Cyclophosphamide treated animals. On the next day after end of chemotherapy course animals were euthanized and total blood plasma from both mice groups was taken. After isolation total fraction of blood plasma DNA was stored at −20° C. in phosphate buffer.

Five groups of mice that were transplanted with LLC tumor participated in experiment.

Group 1-7 mice (control).

Group 2-6 mice intravenously treated with Doxorubicin chemotherapy from $3^{rd}$ up to $8^{th}$ day at 2 mg/kg dose daily.

Group 3-6 mice intravenously treated with Doxorubicin chemotherapy from $3^{rd}$ up to $8^{th}$ day at 2 mg/kg dose daily+intravenous administration of DNA fraction from mice previously subjected to Doxorubicin chemotherapy (0.05 mkg of DNA in 200 mkl of phosphate buffer at day 1 and day 3 after initiation of treatment)

Group 4-6 mice intravenously treated with Doxorubicin chemotherapy from $3^{rd}$ up to $8^{th}$ day at 2 mg/kg dose daily+intravenous administration of DNA fraction from mice previously subjected to cyclophosphamide chemotherapy (0.05 mkg of DNA in 200 mkl of phosphate buffer at day 1 and day 3 after initiation of treatment)

Group 5-6 mice intravenously treated with Doxorubicin chemotherapy from $3^{rd}$ up to $8^{th}$ day at 2 mg/kg dose daily+intravenous administration of DNA fraction from mice previously subjected to Doxorubicin chemotherapy (0.05 mkg of DNA in 200 mkl of phosphate buffer at day 1 and day 3 after initiation of treatment)+intraperitoneal administration of DNase I at 0.5 mg/kg dose for 4 times a day at the first and second days of treatment.

Tumor's size on the $8^{th}$ day after transplantation.

| Group | Tumor's size |
|---|---|
| 1 | 127 +/− 13 |
| 2 | 67 +/− 7 |
| 3 | 115 +/− 20 |
| 4 | 75 +/− 11 |
| 5 | 82 +/− 9 |

So administration of blood plasma DNA from mice subjected to chemotherapy lead to tumor's resistance to chemotherapeutic treatment. DNase's administration prevents appearance of this effect.

Example 13

Influence of Blood Plasma DNA from C57B1 Mice with Highly Metastatic LLC Strain on Metastasizing of Low Metastatic LLC Tumor Strain in C57B1 Mice and Effect of DNase I LLC tumor was transplanted to 30 C57B1 mice. Twenty mice were transplanted with highly metastatic strain and 10 mice were transplanted with low metastatic strain. On the 9th day animals were euthanized and total blood plasma of both mice groups was collected. After isolation the total fraction of blood plasma DNA was stored at −20° C. in phosphate buffer.

Five groups of mice with transplanted LLC tumor participated in the experiment.

1 Group-6 mice transplanted with low metastatic LLC strain.

2 Group-6 mice transplanted with low metastatic LLC strain+intravenous administration of total DNA fraction from mice with transplanted highly metastatic strain (0.05 mkg of DNA in 200 mkl of phosphate buffer on the $7^{th}$ and $8^{th}$ day after transplantation).

3 Group-6 mice transplanted with low metastatic LLC strain+intravenous administration of total DNA fraction from mice with transplanted low metastatic strain (0.05 mkg of DNA in 200 mkl of phosphate buffer on the $7^{th}$ and $8^{th}$ day after transplantation)

4 Group-6 mice transplanted with low metastatic LLC strain+intravenous administration of total DNA fraction from mice with transplanted highly metastatic strain (0.05 mkg of DNA in 200 mkl of phosphate buffer on the $7^{th}$ and $8^{th}$ day after transplantation)+intraperitoneal administration of DNase I at 1 mg/kg dose two times daily at $7^{th}$ and $8^{th}$ day after transplantation.

5 Group-6 mice transplanted with highly metastatic LLC strain.

Number of metastatic foci in lungs was estimated on the $15^{th}$ day after transplantation (N).

Experiments' results are presented in the table.

| Group | N |
|---|---|
| 1 | 12, 0 |
| 2 | 24, 1 |
| 3 | 14, 6 |
| 4 | 11, 6 |
| 5 | 33, 6 |

Received data indicates that blood plasma DNA from mice with highly metastatic LLC strain intensify metastasizing of low metastatic LLC strain.

DNase administration prevents appearance of this effect.

Example 14

DNase I Influence on Life Span of C57B1 Mice Transplanted with LLC Tumor (Highly Metastatic Strain)

Five groups of LLC transplanted mice participated in the experiment.

Group 1-7 mice (control).

Group 2-6 mice were treated with intraperitoneal administration of DNase at 1 mg/kg dose two times a day starting from 3 up to 7 day after tumor transplantation.

Group 3-6 mice were treated with intraperitoneal administration of DNase at 1 mg/kg dose two times a day starting from 3 up to 10 day after tumor transplantation.

Group 4-6 mice were treated with intraperitoneal administration of DNase at 1 mg/kg dose two times a day starting from 3 up to 15 day after tumor transplantation.

Group 5-6 mice were treated with intraperitoneal administration of DNase at 1 mg/kg dose two times a day starting from 3 up to 18 day after tumor transplantation.

Results of experiment were estimated according to animals' survival on the 30 and 50 day after tumor transplantation.

| Group | 30 day (number of alive\number of dead in group) | 50 day (number of alive\number of dead in group) |
| --- | --- | --- |
| 1 | 0-7 | 0-7 |
| 2 | 0-6 | 0-6 |
| 3 | 3-6 | 0-6 |
| 4 | 5-1 | 3-3 |
| 5 | 6-0 | 6-0 |

The significant inhibition of tumor's growth was observed at the last day of DNase treatment in the 2nd and 3rd groups, but tumor's growth renewed after DNase withdrawal and to the $25^{th}$ day size of tumor in this groups and in control has equalized.

The most longitudinal course of DNase treatment (from $3^{rd}$ up to 18th day-group number 6) has lead to maximal survival. Inhibition of tumor growth was more than 95% at day 18.

In all experiments single and multiple injection of up to 2.5 mg/kg of human DNase I (maximal dose that was used in experiments) had no toxic effect on animals.

So, DNase I does not cause direct cytotoxic effect on tumor cells (in our in vitro experiments at concentration of 100 mkg/ml) and experimental data confirm that antitumor effect is connected with destruction of DNA in blood plasma and DNase's therapeutic effect increases with increasing of its treatment course duration.

Example 15

Influence of Different Methods of Blood Plasma DNA's Destruction, Inactivation, and Binding on Ability of Blood Plasma DNA from C57B1 Mice with Transplanted Highly Metastatic LLC Strain to Intensify Metastasizing of Low Metastatic LLC Tumor Strain in C57B1 Mice 100 mice were transplanted with highly metastatic LLC strain. On the 9th day after transplantation, animals were euthanized and total blood plasma was taken. After isolation total fraction of blood plasma DNA was stored at −20° C. in phosphate buffer.

Six groups of mice with transplanted low metastatic LLC strain participated in the experiment.

Group 1-6 mice transplanted with low metastatic LLC strain.

Group 2-6 mice transplanted with low metastatic LLC strain+two intravenous injections of total DNA fraction from mice transplanted with highly metastatic strain on the 7th and 8th day after transplantation (0.05 mkg of DNA was dissolved in 500 mkl of fresh heparinized blood before injection).

Group 3-6 mice transplanted with low metastatic LLC strain+two intravenous injections of total DNA fraction from mice transplanted with highly metastatic strain on the 7th and 8th day after transplantation (0.05 mkg of DNA was dissolved in 500 mkl of fresh blood plasma before injection). Before administration the sample was photochemically disinfected (1 mkM of methylene blue was added with following irradiation by red light during 10 minutes (60 000 Lux).

Group 4-6 mice transplanted with low metastatic LLC strain+two intravenous injections of total DNA fraction from mice transplanted with highly metastatic strain on the 7th and 8th day after transplantation (0.05 mkg of DNA was dissolved in 500 mkl of fresh blood plasma before injection). The sample was passed through the column containing DEAE-cellulose for two times before administration.

Group 5-6 mice transplanted with low metastatic LLC strain+two intravenous injections of total DNA fraction from mice transplanted with highly metastatic strain on the 7th and 8th day after transplantation (0.05 mkg of DNA was dissolved in 500 mkl of fresh heparinized blood before injection). 1 mkg of fragment A of Ricin toxin was added to the sample before administration and sample was incubated at 370 C for 1 hour. Ricin toxin is representative of RIP toxins family (proteins that inactivate ribosomes) which are used for immunotoxin's creation. Besides their ability to inactivate ribosomes these proteins can deadenylate DNA. For realization of toxic effect catalytic subunit A of RIP II type should by delivered to cell by B subunit. Without B subunit A chain is not toxic but can be used for blood plasma DNA's inactivation due to its polynucleotide-adenylglicozidase activity.

Group 6-6 mice transplanted with low metastatic LLC strain+two intravenous injections of total DNA fraction from mice transplanted with highly metastatic strain on the 7th and 8th day after transplantation (0.05 mkg of DNA was dissolved in 500 mkl of fresh heparinized blood before injection. Total DNA fraction was enzymatically methylated before administration (I. Muiznieks et. al., FEBS Letters, 1994, v. 344, pp. 251-254).

Number of metastaic nodules in lungs was estimated on the 15th day after transplantation.

Results of the experiments are presented in the table.

| Group | Ncp. |
| --- | --- |
| 1 | 12, 0 |
| 2 | 22, 5 |
| 3 | 14, 1 |
| 4 | 15, 5 |
| 5 | 15, 1 |
| 6 | 12, 3 |

Received data indicates that all used methods inhibited ability of blood plasma DNA of mice with highly metastatic LLC tumor strain to increase metastasizing process of low metastatic LLC tumor strain.

INDUSTRIAL APPLICABILITY

For the realization the methods there were used well-known materials and equipment manufactured in plant conditions and according to aforesaid the invention conformances to requirements of "industrial applicability" criteria (IA).

What is claimed is:

1. A method for monitoring development of somatic mosaicism in a subject diagnosed with cancer, said method comprising:
   (a) isolating extracellular blood DNA from the blood of said subject at two or more different time points,
   (b) creating a separate DNA library from the extracellular blood DNA isolated at each time point in step (a) by cloning said extracellular blood DNA, wherein each said DNA library has at least $10^6$ clones,
   (c) sequencing multiple DNA clones from each library created in step (b), and
   (d) determining quantitative and qualitative differences between the sequenced clones from the libraries representing different time points.

2. The method of claim 1, wherein the development of somatic mosaicism is a spread of cancer promoting mutations.

3. The method of claim 2, wherein the development of somatic mosaicism is a spread of metastasis promoting mutations.

4. The method of claim 1, wherein the development of somatic mosaicism is a spread of mutations promoting resistance to cancer chemotherapy.

5. The method of claim 1, wherein cloning in step (b) is performed without prior amplification.

* * * * *

SEQUENCE LISTING

<160> NUMBER OF SEQ ID NOS: 155

<210> SEQ ID NO 1
<211> LENGTH: 484
<212> TYPE: DNA
<213> ORGANISM: Homo sapiens

<400> SEQUENCE: 1

| | |
|---|---|
| cgacggccag tgagcgcgcg taatacgact cactataggg cgaattgggt accgggcccc | 60 |
| ccctcgaggt cgacggtatc gataagcttg atatcgaatt ctgaccaccc caaggtggcc | 120 |
| atccttgtcc ctgtgattcc agatctccag aactggaggt ctagcttcag ggaaaaccca | 180 |
| gattttcttg gcttagccca cctgacagct aatcactgga aatggggtgg gctggtagag | 240 |
| tcctttggtc aggttttgtg tcaagagagg gaggaggaaa gatgggaggg aggtagcaaa | 300 |
| actggtctca atggaactat gtaagttaat atagaatggc aaagggatgt ttcttccaag | 360 |
| gaaagaattc ctgcagcccg ggggatccac tagttctaga gcggccgcca ccgcggtgga | 420 |
| gctccagctt ttgttccctt tagtgagggt taattgcgcg cttggcgtaa tcatggtcat | 480 |
| agct | 484 |

<210> SEQ ID NO 2
<211> LENGTH: 244
<212> TYPE: DNA
<213> ORGANISM: Homo sapiens

<400> SEQUENCE: 2

| | |
|---|---|
| gaattctcaa attattactg aggaaaatgt gacagtgctt caaagcagta gtaattttt | 60 |
| ctcattatgc tgcatttatt attaaaacca acagtggaca gtgaatgact aactgatcct | 120 |
| tttttgggaa tattacttcc aaatgaacgt taacttaaag attggaatat gaacacacta | 180 |
| ttgcttttac actagagagg ttactcctgg ccactctttc agcagcagtt agcttcagga | 240 |
| attc | 244 |

<210> SEQ ID NO 3
<211> LENGTH: 230
<212> TYPE: DNA
<213> ORGANISM: Homo sapiens

<400> SEQUENCE: 3

| | |
|---|---|
| gaattcgcag taacttcctt gtgttgtgtg tattcaactc acagagttga acgatcgttt | 60 |
| acacagagca gacttgaaac actcttttg tggaatttca agtggagatt tcaattgttt | 120 |
| gaggtcaatg gtagaatagg aaatatcttg ctatagaaac tagacagaat gattctcaga | 180 |
| aactcctttg tgatgtgtgc cttcaactca cagagtttaa cctttctttt | 230 |

<210> SEQ ID NO 4
<211> LENGTH: 218
<212> TYPE: DNA
<213> ORGANISM: Homo sapiens

<400> SEQUENCE: 4

| | |
|---|---|
| gaattctcat gaaattgaaa tgatggact catcatcgaa tggattcgaa tggaatcatc | 60 |
| gaataaaatt gattgagaat catcatcaaa tggaatcgaa tggtatcatt gaatggaatc | 120 |
| gaatggaatc atcatcagat ggaaatgaat ggaatcgtca tagaatccaa tcgaatggat | 180 |
| tcattgaatg gaatcagatg gaatcatcga gtgactga | 218 |

```
<210> SEQ ID NO 5
<211> LENGTH: 182
<212> TYPE: DNA
<213> ORGANISM: Homo sapiens

<400> SEQUENCE: 5
gaattctcta cagggacaga actaatggaa tatatgtatt atacagggga gtttattaaa      60
cattaactca catgatcaca aggtcccgca ataggctgtc tgcaggcagg ggcgaaggag     120
gccagtgaag ttccaaaact caagaaccta gagtcaatgt tcaagggcga ggaagcatcc     180
ag                                                                    182

<210> SEQ ID NO 6
<211> LENGTH: 152
<212> TYPE: DNA
<213> ORGANISM: Homo sapiens

<400> SEQUENCE: 6
gaattcacag aaatcattgc cacaggcaag atctgatgaa ccttgatgaa tgctaaaatt      60
agttggtgaa agtttaagca gaaacagaat gtttgcatag aatgaagcaa agaaggaaa     120 aaaaattatg agcccttgat ttagggtct tt                                   152

<210> SEQ ID NO 7
<211> LENGTH: 131
<212> TYPE: DNA
<213> ORGANISM: Homo sapiens

<400> SEQUENCE: 7
gaattcttct gtctagagta acatgaagaa atcccgtttc caacgaaggc cctcaaggcg      60
gtcaattatc cacttcgaga ttctacagaa agagtgtttc aaaactgctc tatcaagaga     120
aatgttccac c                                                          131

<210> SEQ ID NO 8
<211> LENGTH: 239
<212> TYPE: DNA
<213> ORGANISM: Homo sapiens

<400> SEQUENCE: 8
gaattcccag taacttcctt gtgttgtgta cattcaactc acagagttga acgttccctt      60
agacagagca gatttgaaac actcttttg tgcaattggc aagtggagat ttcaagcgct     120
ttaaggtcaa tggcagaaaa ggaaatatct tcgtttcaaa actagacaga atcattccca     180
caaactgcgt tgtgatgtgt tcgttcaact cacagagttt aacctttctt ttcatagag     239

<210> SEQ ID NO 9
<211> LENGTH: 207
<212> TYPE: DNA
<213> ORGANISM: Homo sapiens

<400> SEQUENCE: 9
gaattctcta gacttccttg ggtttagcgc tgagtgaaga ggcacggaga gggtttggag      60
ctttagggta aagcactgat ggaagaaagg aattcctgca gcccggggga tccactagtt     120
ctagagcggc cgccaccgcg gtggagctcc agcttttgtt ccctttagtg agggttaaaa     180
gcgcgcttgc gtaatcatgg tcatagc                                        207

<210> SEQ ID NO 10
<211> LENGTH: 223
<212> TYPE: DNA
```

<213> ORGANISM: Homo sapiens

<400> SEQUENCE: 10

| gaattcatcg ctaggactgt gttcttgttt attgggatgg aagggagag aaaagatgag | 60 |
| agggcaaaa gagaaaattt tggaaaatga gaaacttact ttattgcact gtctgtgcaa | 120 |
| ttgttggtct taaggaacaa atacactaaa ttcaaagatg ataaaaaaaa aaaacagctt | 180 |
| cacagagctg tagtaaacac cagatgttga aagagaagcg tat | 223 |

<210> SEQ ID NO 11
<211> LENGTH: 198
<212> TYPE: DNA
<213> ORGANISM: Homo sapiens

<400> SEQUENCE: 11

| gaattccatt tgatgacaat tccattcaat accaattgat gatgtttatt tttgattcca | 60 |
| tttgatgatg attacattcg attccatttc atcatgattc cattcgattc cactcgatga | 120 |
| ttccattcga ttccattcaa tgattattcc acttgagtcg attcgatgac tccattcgat | 180 |
| tgtattcgat ggtgattg | 198 |

<210> SEQ ID NO 12
<211> LENGTH: 217
<212> TYPE: DNA
<213> ORGANISM: Homo sapiens

<400> SEQUENCE: 12

| gaattctgcc aagcagtgac ttgattcatg aacactcact ggatgctgac tctgttgctc | 60 |
| ttctgagtgc tggggtagag gagaggatga ggtggacgca cagttcttgc ttttatgagc | 120 |
| ttatgttcta ggaaattcaa acaagtattt tttcaggcag gtagtatgaa atagcaggaa | 180 |
| gaggaagcag gctaaaggga cacagagtga ttggggg | 217 |

<210> SEQ ID NO 13
<211> LENGTH: 223
<212> TYPE: DNA
<213> ORGANISM: Homo sapiens
<220> FEATURE:
<221> NAME/KEY: modified_base
<222> LOCATION: (129)..(129)
<223> OTHER INFORMATION: a, c, t or g

<400> SEQUENCE: 13

| gaattcaggg ctgcagaaat ttgtgtaagt aaagaggagc agaatgttaa tagccaagac | 60 |
| aatgcaaaaa atgcattcaa ggtgttttga aaccttcatg gtagcccctc ccattacaag | 120 |
| cctggaggnc tgggagggaa aaataatccc tgaaccagga caagggccct atccctattt | 180 |
| ctctgtacag tctcaggaca cagcactttg catcccagca gct | 223 |

<210> SEQ ID NO 14
<211> LENGTH: 258
<212> TYPE: DNA
<213> ORGANISM: Homo sapiens

<400> SEQUENCE: 14

| gaattcgctt acagtcagtt acaaatgctt tttagatctt caatgcttct gtgaagcctc | 60 |
| atatttgctg ttcagacaga cactataatg gagatggaat aaatggacag caactacaca | 120 |
| ggacggtgtg gcagatggt gttggagcga ggggtgcagg tggagcccac aggagaggaa | 180 |
| ggctgattga tcttctatgg ggagagcttc atagcacggg ggtggggcac acctgactgg | 240 |

```
caagctgttt ggtgtgag                                                  258
```

<210> SEQ ID NO 15
<211> LENGTH: 239
<212> TYPE: DNA
<213> ORGANISM: Homo sapiens

<400> SEQUENCE: 15

```
gaattctttt gaactagctg tgttttgaca gaggtttttt tttttttttt tctttttttg    60
gttttttgct tctctgacaa aggcctttgg aagaatgagc ttcttccccc acatctttat   120
ttatttattt attttttaagc tatgctcagg aaaatgaaca tttctccttt gcagttgata  180
acagcattta caaggtatac agcatatagg gttgttccaa attccttccc agataacca    239
```

<210> SEQ ID NO 16
<211> LENGTH: 236
<212> TYPE: DNA
<213> ORGANISM: Homo sapiens

<400> SEQUENCE: 16

```
gaattcctga atggtggggg gactgtgtgt ctctggccct attccctctc caggacaaac    60
ctcaccctt cctgcaaatg tactcaaaat agtacattta tccacgtcaa ttcagcaaag   120
gctgcagatc ctgggactac agtatctcag acgctgttct cagcgagctc atggtccagt  180
ggagagcaca gacaaacagc aaggcaggag aaatcgcctc tgaagagccc agggag       236
```

<210> SEQ ID NO 17
<211> LENGTH: 156
<212> TYPE: DNA
<213> ORGANISM: Homo sapiens

<400> SEQUENCE: 17

```
gaattcagcc gtggcagtga gatggagtgt gtgtttagaa ctgttgattg atctggctct    60
ccctgattag gaggccgaga tcgagactcg gattgctgag ctgcggaagg agggtttctg  120
gtcactgaag aggctgccta aggtgccaga gccccc                              156
```

<210> SEQ ID NO 18
<211> LENGTH: 191
<212> TYPE: DNA
<213> ORGANISM: Homo sapiens

<400> SEQUENCE: 18

```
gaattctaca aaagaaataa agcagagatg tgaaaggaat ttcttcaact atacacattt    60
tgacataatc atcttctaac atggtgttta atttgctctg cttcacttag caatgatata  120
atgaatattt cccattttat tatatattct acaatatcac tttgaatgac tctcttaaga  180
gtgtattata c                                                        191
```

<210> SEQ ID NO 19
<211> LENGTH: 312
<212> TYPE: DNA
<213> ORGANISM: Homo sapiens

<400> SEQUENCE: 19

```
cgacggccag tgagcgcgcg taatacgact cactataggg cgaattgggt accgggcccc    60
ccctcgaggt cgacggtatc gataagcttg atatcgcttg tgggctgaag gatgcaattc   120
tagacagagt tagctgggaa tgcctcactg agaagggggcc atttgagtaa aggcctgaaa  180
```

```
aggtgaagaa gaattcctgc agcccggggg tccactagtt ctagagcggc cgccaccgcg      240
gtggagctcc agcttttgtt ccctttagtg agggttaatt gcgcgcttgg cgtaatcatg      300
gtcatagctg tt                                                          312

<210> SEQ ID NO 20
<211> LENGTH: 219
<212> TYPE: DNA
<213> ORGANISM: Homo sapiens

<400> SEQUENCE: 20
gaattccagt ggaatcagtt gtaatgtctc cttttttcata tctgatttta tttagtgtct      60 tttttttctta gatagtcttg ctaaaggttt ctcaatttat cttttcaaaa aatcttttca    120
ttttgttgat cttttttatt attttcttca tttcattttt atttatttct gctctgatct     180
ttattatttc ttttcttcta ataattttgg gtttagttt                             219

<210> SEQ ID NO 21
<211> LENGTH: 208
<212> TYPE: DNA
<213> ORGANISM: Homo sapiens

<400> SEQUENCE: 21
gaattctcag taacttcctt gtgttgtgtg tattcaactc acagagttga acgatccttt       60
acacagagcg gacttgaaac actcttttg tggaatttgc aagtgagat ttcagccgcg      120 ttgaggtcaa tggtagaaaa ggaaatatct tcgtataaaa actagacaga atgattctca    180
gaaactcctt tgtgatgtgt gtgttcaa                                        208

<210> SEQ ID NO 22
<211> LENGTH: 262
<212> TYPE: DNA
<213> ORGANISM: Homo sapiens

<400> SEQUENCE: 22
gaattcaatg gaatggaatg gacaggaatg gaatggaatg gaaaggaatg gagtggaatg       60
gactagaatg gaatggaatg gaatgaaatc aacccgattg gaatggaatg gaatgcaatg     120
gaatggaatg gaatcaactg gaaaggaatc aaatagaacg gaatggaata gaatggaatg    180
gattggaatg gaatggaatg gattcaaccc gagtggaatg gaatggaata gaatggaata    240
aacaacgagt ggaatggaat gg                                              262

<210> SEQ ID NO 23
<211> LENGTH: 218
<212> TYPE: DNA
<213> ORGANISM: Homo sapiens

<400> SEQUENCE: 23
gaattcgttg aggagcttct ggaaagtgca cattctgact cagcaggtat tggagtctgc       60
atttctcatg agcactcagg tgatgaaaga gctggtcctt ggacacagct ctgaatagca    120
agggaatagc tttcctttag agaaatctgg aaaaagaacc actggagagc aatttaaaaa    180
ataacagaat ccagggaaag ctttaatttc cttttatt                             218

<210> SEQ ID NO 24
<211> LENGTH: 213
<212> TYPE: DNA
<213> ORGANISM: Homo sapiens

<400> SEQUENCE: 24
```

```
gaattcaaag gaatcatcat caaatagaac cgaatggaat cctcattgaa tggaaatgaa    60
aggggtcatc atctaatgga atcgcatgga atcatcatca aatggaatcg aatggaatca   120
tcatcaaatg gaatcgaatg gaatcatcat caaatggaat ctgatggaat cattgaacag   180
aattgaatgg aatcgtcatc gaatgaattg aat                                213

<210> SEQ ID NO 25
<211> LENGTH: 229
<212> TYPE: DNA
<213> ORGANISM: Homo sapiens

<400> SEQUENCE: 25
gaattctgtg cgtatttag aagtagaatt ataagatttg tggatatgtt agttttggag     60
tgtgaggtca aaggcgtttt gagcaacttg taagaaacca tttttaaggc ggaagtcggg   120 aatttttgttt tttatatgtt gaatttgaaa tccttattaa acatccaagt ggagaggctg   180
gatagacaat taaatttaga ccctgaggtt cgggaaggaa gtccaatgg                229

<210> SEQ ID NO 26
<211> LENGTH: 216
<212> TYPE: DNA
<213> ORGANISM: Homo sapiens

<400> SEQUENCE: 26
gaattcttca agaaacatca aggagggatg tatagatagt ttttaaaaa accgaaatgt     60 aaagaaata caagaagaat ggaaacatct acataacgag agtggaaaga atgaaaata    120 gaggtagata gattagatag atagatagat agatagattg attgatggat tgatagattg   180
atagatatag aaataaaaga aagaaaatag aagatg                              216

<210> SEQ ID NO 27
<211> LENGTH: 244
<212> TYPE: DNA
<213> ORGANISM: Homo sapiens

<400> SEQUENCE: 27
gaattccaat gcaatgttaa acagaaagca gcccttttt tcaaaattta taggcaaggt      60
gtttaacata tggctaaata atgttaattt atagtaaata tccttcataa ggatgaagat   120
gtacccttct attttagttt gctgagtgtc ttttagtcat aattgagtgt tgacatctgt   180
caaatatttt ttctgcatct attaagacat ccatgtgata tttctctttt attctcttac   240
tatg                                                                 244

<210> SEQ ID NO 28
<211> LENGTH: 237
<212> TYPE: DNA
<213> ORGANISM: Homo sapiens

<400> SEQUENCE: 28
gaattcaatc accatcgaat acaatcgaat ggagtcatcg aatcgactca agtggaataa     60
tcattgaatg gaatcgaatg gaatcatcga gtggaatcga atggaatcat gatgaaatgg   120
aatcgaatgt aatcatcatc aaatggaatc aaaaataaac atcatcaatt ggtattgaat   180
ggaattgtca tcaaatggaa ttcctgcagc ccgggggatc cactagttct agagcgg       237

<210> SEQ ID NO 29
<211> LENGTH: 184
<212> TYPE: DNA
```

<213> ORGANISM: Homo sapiens

<400> SEQUENCE: 29

```
gaattctttc cagaaggttt ttaatttact ttgctcggct ccatcagggg aatcactatg    60
gcagctatag ccttaagaaa tttatttctt aaataagact tgagagtcag aattgcttct   120
ttatccatgg tctcgaggat gggatgttgt gatagcaggc gtgaaaacaa cattcatctc   180
ctgg                                                                184
```

<210> SEQ ID NO 30
<211> LENGTH: 191
<212> TYPE: DNA
<213> ORGANISM: Homo sapiens

<400> SEQUENCE: 30

```
gaattcagaa tctggatggc aaggaagcgc atcaagatgc aggagaaagt tgaaacctaa    60
tccaaggaat acagtaaaac aatccagaag cttgaaagac aaaatagcca ttttaagaac   120
caaactgagc ttctggaagg gaaaaattta cttcaagaat tcataatac  aatcaaaagt   180
atttttttt t                                                         191
```

<210> SEQ ID NO 31
<211> LENGTH: 143
<212> TYPE: DNA
<213> ORGANISM: Homo sapiens
<220> FEATURE:
<221> NAME/KEY: modified_base
<222> LOCATION: (48)..(48)
<223> OTHER INFORMATION: a, c, t or g

<400> SEQUENCE: 31

```
gaattccgct tggggaggga actgtcttcg tccaggaaaa tgtttttnat aagccaccca    60
tggtaaaagg agaagtcatg acggttaggg tgttggcagg aatcaaatta agaaaaggaa   120
tggctatcca tccggttgta tgt                                           143
```

<210> SEQ ID NO 32
<211> LENGTH: 169
<212> TYPE: DNA
<213> ORGANISM: Homo sapiens

<400> SEQUENCE: 32

```
gaattctaga ctgctgcacc tccatatcct cagcaactgg catgatgatg agcagggagt    60
tagtagaact aatacactaa tatgtaaatg aatgaatgaa tgtttcctga gtgtggcttt   120
aagtttctca gaagaagaca gttcatacac tggtgcataa aattctggg              169
```

<210> SEQ ID NO 33
<211> LENGTH: 124
<212> TYPE: DNA
<213> ORGANISM: Homo sapiens

<400> SEQUENCE: 33

```
gaattctagg acaaggtgat tgtcctagat tttctcttaa acgcctcctg ttagatagga    60
aatggccatt aatagagaag cttgcttgag ggagtaaccc tgaaagccca ggcctggaca   120
cccg                                                                124
```

<210> SEQ ID NO 34
<211> LENGTH: 214
<212> TYPE: DNA
<213> ORGANISM: Homo sapiens

<400> SEQUENCE: 34
gaattctaag tttatatagg ttacaacatc acagtaagaa tgtcacagag gggtatatgc    60
ttttcatcaa acaacaaatt gaaaatttt taactcttaa ggactgattt tgcttaacta    120
caagttatgc actgatggta gtagcttcat aaatttagaa aagttccaaa ataatgctta   180
gaaagagtag ctatttaact tctcattgaa caaa                                214

<210> SEQ ID NO 35
<211> LENGTH: 164
<212> TYPE: DNA
<213> ORGANISM: Homo sapiens

<400> SEQUENCE: 35
gaattcctgt gaatgtcgtt tcaaatatta ctcagcctac gcactgacca gaacttattt    60
tttacagaat cattttgaca ggaaaagtgt ttatgatagt tttgttgttg ttgttgttgt   120
tttgtttttt catcacccag gctgcttcac atttagagct gagt                     164

<210> SEQ ID NO 36
<211> LENGTH: 119
<212> TYPE: DNA
<213> ORGANISM: Homo sapiens
<220> FEATURE:
<221> NAME/KEY: modified_base
<222> LOCATION: (88)..(88)
<223> OTHER INFORMATION: a, c, t or g

<400> SEQUENCE: 36
gaattctgag aactagccct ttaagactgg tggagattta ttcaggaggg aagccctgcc    60
ccagggaaaa gttgccaaga gacttgtntt taggagatca ccagcccaaa tttccatga   119

<210> SEQ ID NO 37
<211> LENGTH: 208
<212> TYPE: DNA
<213> ORGANISM: Homo sapiens

<400> SEQUENCE: 37 gaattcccttt catattttg gtcaaagccc agttttctg agtcggtggg ctaaatggga    60
ttactctttc taatgaggca tccttgtgtg cttagaatca ctcttgactt tatcctgtcc   120
ccctcgggtt cctaacttac caggatggag agcatttcct cattccatgt tgtgggagg    180 ttggcccact gggtgacatc agcccagg                                       208

<210> SEQ ID NO 38
<211> LENGTH: 169
<212> TYPE: DNA
<213> ORGANISM: Homo sapiens

<400> SEQUENCE: 38
gaattcctta acccttaatt agctttggtt tttgctcaat atcctgaagc tgggcacagt    60
ctcaatgtaa ctattctcct aggggctgaa ctgggtgcta gtcatcaaag tttggaatgt   120
cattttagaa gcaacctcta gaagtaatcc tggtaagccc tagaagtaa                169

<210> SEQ ID NO 39
<211> LENGTH: 172
<212> TYPE: DNA
<213> ORGANISM: Homo sapiens

<400> SEQUENCE: 39

```
gaattcccat cttttttgt gtgtgtgttt gagactgtat tttgcattgt cgtccacact      60
ggagtacagt ggcgtgatct ccgctcgctg caagctccgc ctcatggatt taagcgattc    120
tcctgcctca gcctcccaag tggctgggac tacaggtgcc cgaccaacca cg            172
```

<210> SEQ ID NO 40
<211> LENGTH: 137
<212> TYPE: DNA
<213> ORGANISM: Homo sapiens
<220> FEATURE:
<221> NAME/KEY: modified_base
<222> LOCATION: (124)..(124)
<223> OTHER INFORMATION: a, c, t or g

<400> SEQUENCE: 40

```
gaattctgtt acttggtgat gggaaaccgt gaaggtttta agcaagactg tgatgtgctt     60
aggtttatta gaaggttcta tgctgctcag cctccctgtc tagttctttg ctttattgac    120
tgtntcctca ctaaatg                                                    137
```

<210> SEQ ID NO 41
<211> LENGTH: 152
<212> TYPE: DNA
<213> ORGANISM: Homo sapiens

<400> SEQUENCE: 41

```
gaattctttt ttccccagct ttatggagat ttaattgaca aataaaatgg catatattta     60
ggtgtatata tttgatatat gtatacattg tgaaacgatt actataatga agttaattaa    120
catattcctc atcttgcata gtcaccattt tt                                  152
```

<210> SEQ ID NO 42
<211> LENGTH: 183
<212> TYPE: DNA
<213> ORGANISM: Homo sapiens

<400> SEQUENCE: 42

```
gaattctcca tgaaaacaga catatttgat atttaggtgc tttaatggac cctgaaaaga     60
aattagattg attcatttga agaataaatg tcggtccccc gccctctaca tggtaaaact    120
cttccaaatg cttctactta atggaaatgg aaattacctc tcaaaacatt acaaaaacta    180
atg                                                                  183
```

<210> SEQ ID NO 43
<211> LENGTH: 162
<212> TYPE: DNA
<213> ORGANISM: Homo sapiens
<220> FEATURE:
<221> NAME/KEY: modified_base
<222> LOCATION: (43)..(43)
<223> OTHER INFORMATION: a, c, t or g

<400> SEQUENCE: 43

```
gaattccgac cactgctgac cgccaggcca cacaccggtt ttnttcagga ggtctcaact     60
agatgctaag ctccgaagtg gaactccctc aggcactttc tgttctaatt caggaattcc    120
tcgagcccgg gggatccact agttctagag cggccgccac cg                       162
```

<210> SEQ ID NO 44
<211> LENGTH: 189
<212> TYPE: DNA
<213> ORGANISM: Homo sapiens

<400> SEQUENCE: 44

```
gaattctgtg aaataattct cagcccagac ccaagggatc cacagctcag aaataggtta    60
tccagaagtg ttcctaacac tagatgacag tatcccagtg ctccaaacca gcttattact   120
tggccagaat tcctgcagcc cggggatcc actagttcta gagcggccgc caccgcggtg    180
gagctccag                                                           189
```

<210> SEQ ID NO 45
<211> LENGTH: 190
<212> TYPE: DNA
<213> ORGANISM: Homo sapiens

<400> SEQUENCE: 45

```
gaattctctg tctgtcgatt tcagtgattt tagtgctggt cctccacttg agtactagcc    60
ataggtcttg gcttggcact cccatcccat agccctgtgc accatagctc tggggtgaac   120
tcaggcaaaa cgattttcgt ccccagcttg ggagcagcag ggttggggac cttggcaatg   180
gcaatggcag                                                          190
```

<210> SEQ ID NO 46
<211> LENGTH: 266
<212> TYPE: DNA
<213> ORGANISM: Homo sapiens

<400> SEQUENCE: 46

```
gtaatacgac tcactatagg gcgaattggg taccgggccc cccctcgagg tcgacggtat    60
cgataagctt gatatcggct tatcctgagc taggctgagc ctttgctctc ctgacctagt   120
tagttctcat tcaaccctgt gacaagggat gtggggctca gagaacggga gggtcttccc   180
tcaggtcaca tggccagggc atggagaggc aggacttgaa tccaggtcaa tgtgacccca   240
gagcctagtg tggaaacccg tccttt                                        266
```

<210> SEQ ID NO 47
<211> LENGTH: 164
<212> TYPE: DNA
<213> ORGANISM: Homo sapiens
<220> FEATURE:
<221> NAME/KEY: modified_base
<222> LOCATION: (81)..(81)
<223> OTHER INFORMATION: a, c, t or g

<400> SEQUENCE: 47

```
gaattctacc ctgggtagga tagtagctcc cctcaacttt acagcaaata cagctaacct    60
tgctttacct gcgatcccgt ntttattttg ttgaattaga gaaactgagg gaagcagttc   120
tctacactca ctttacccctt agagccctct acaatcaacc ctgt                   164
```

<210> SEQ ID NO 48
<211> LENGTH: 112
<212> TYPE: DNA
<213> ORGANISM: Homo sapiens
<220> FEATURE:
<221> NAME/KEY: modified_base
<222> LOCATION: (16)..(16)
<223> OTHER INFORMATION: a, c, t or g
<220> FEATURE:
<221> NAME/KEY: modified_base
<222> LOCATION: (36)..(36)
<223> OTHER INFORMATION: a, c, t or g
<220> FEATURE:
<221> NAME/KEY: modified_base
<222> LOCATION: (40)..(40)
<223> OTHER INFORMATION: a, c, t or g

<400> SEQUENCE: 48
gaattcaaag actgtnagat gtaagcagtg actganacan aggcaatgag atgagaggtg    60
gaaaggagac caaatgtaaa agacagcaga aacttgagtg gacggtggca ca          112

<210> SEQ ID NO 49
<211> LENGTH: 114
<212> TYPE: DNA
<213> ORGANISM: Homo sapiens
<220> FEATURE:
<221> NAME/KEY: modified_base
<222> LOCATION: (52)..(52)
<223> OTHER INFORMATION: a, c, t or g
<220> FEATURE:
<221> NAME/KEY: modified_base
<222> LOCATION: (57)..(57)
<223> OTHER INFORMATION: a, c, t or g
<220> FEATURE:
<221> NAME/KEY: modified_base
<222> LOCATION: (61)..(61)
<223> OTHER INFORMATION: a, c, t or g
<220> FEATURE:
<221> NAME/KEY: modified_base
<222> LOCATION: (74)..(74)
<223> OTHER INFORMATION: a, c, t or g

<400> SEQUENCE: 49
gaattctgtt ggctttacct ttaacgtgtc caaaagtgac caattatcat tnctgcnttt    60
ngctgctact tggntcaagc cattagtatc ccttgctcca ataaactctt tcct         114

<210> SEQ ID NO 50
<211> LENGTH: 206
<212> TYPE: DNA
<213> ORGANISM: Homo sapiens

<400> SEQUENCE: 50
gaattcccag taacttcctt gtgttgtgtg tgttcaactc acagagttga actttcattt    60
acacagagca gatttgaaac actcttttg tggaatttgc aaatggagaa ttcctgcagc   120
ccgggggatc cactagttct agagcggccg ccaccgcggt ggagctccag cttttgttcc   180
ctttagcgag ggttaattgc gcgctt                                        206

<210> SEQ ID NO 51
<211> LENGTH: 169
<212> TYPE: DNA
<213> ORGANISM: Homo sapiens

<400> SEQUENCE: 51
ccccccctcg aggtcgacgg tatcgataag ctggatatcg gcaacttctc gctctgtcct    60
cacataggga agaggaagc tgttgccttc ctcttacaag agcactaatc tcacatgggt   120
gtttaccctc atgactttat ctaaacctaa ttatctttca aagaatcta               169

<210> SEQ ID NO 52
<211> LENGTH: 141
<212> TYPE: DNA
<213> ORGANISM: Homo sapiens

<400> SEQUENCE: 52
gaattcttgt tttcagtgaa aatttagata atttatctca ggaattcctg cagcccgggg    60
tttccactag ttctagagcg gccgccaccg cggtggagct ccagcttttg ttccctttag   120
ttagggttaa ttcgcgcttg c                                             141

<210> SEQ ID NO 53
<211> LENGTH: 203
<212> TYPE: DNA
<213> ORGANISM: Homo sapiens

<400> SEQUENCE: 53

```
gaattctata tatttcccct cttttcctga ctcttcagtg acaatcctaa gaccgtgcta    60
ataacagaag acagtaatcc cttttttag  ccaaataatt tggaagccat gattttcttt   120
gcatatcatg aaagtgacca tggtgttgga tattgtgggt agaagctttc aagtaaaaaa   180
gaactgtcat tcaactgaat tgg                                           203
```

<210> SEQ ID NO 54
<211> LENGTH: 162
<212> TYPE: DNA
<213> ORGANISM: Homo sapiens

<400> SEQUENCE: 54

```
gaattctagg ccaggcgcga tggttcacac ctgtaatccc agcatttcc cgggaagcca    60 aggcaggcag atcacttgag gccaagagtt caagaccaac ctggccaaag gggtgaaatc   120
catctctact aaaaatacaa aaattagtcg ggcgcggcgg cg                      162
```

<210> SEQ ID NO 55
<211> LENGTH: 193
<212> TYPE: DNA
<213> ORGANISM: Homo sapiens

<400> SEQUENCE: 55

```
gaattctatt tctaggaacg ttctcaaaca agcttaagag caaagtataa aaacgatgtt    60
cagcatataa taatatgaaa aaattttgtc ctagacattt tatatgaaaa tgtatacttt   120
agagcatgct tcaggaaaaa aagaaagaaa aattaatcct gggaaatggg tgacattaga   180
tacaggcgag tgg                                                      193
```

<210> SEQ ID NO 56
<211> LENGTH: 169
<212> TYPE: DNA
<213> ORGANISM: Homo sapiens

<400> SEQUENCE: 56

```
gaattctgct tttatgagaa gtcagctgaa tgctatggaa aggagtatag agagtggctt    60
aaaagtttca ggcaagttca caccaaaact tgcattctaa cctccctgaa cctgtggtct   120
agaagggacc tatcagcaag atgataacca aaaatgtcta gaatctgag               169
```

<210> SEQ ID NO 57
<211> LENGTH: 141
<212> TYPE: DNA
<213> ORGANISM: Homo sapiens

<400> SEQUENCE: 57

```
gaattctaga gaacaatccc tactgacttc acacacaact taagaaatgc aagtaaaggg    60
ccgggcgcgg tggcccagca cctgtaatcc cagtactttg ggagcctaga ggcaggtggt   120
cattggaagt caggagttca a                                             141
```

<210> SEQ ID NO 58
<211> LENGTH: 183
<212> TYPE: DNA
<213> ORGANISM: Homo sapiens

<400> SEQUENCE: 58

```
gaattctctg atgtttagtt aggtatgacc tacagttaaa ggctttgctg cattccttac    60
gtttgtaggg tttctctccg gtatgactac ttcgatgtcg agtaacggac gttgaattac   120
gataaaaggc tttgccacat tctttgcatt tatagggttt ttctccagta tgaattccag   180
cag                                                                 183
```

<210> SEQ ID NO 59
<211> LENGTH: 185
<212> TYPE: DNA
<213> ORGANISM: Homo sapiens

<400> SEQUENCE: 59

```
gaattctatc aatgtcaatt aaatccagtt gatggatggc cataatttta aatctattta    60
cattttgggg tattttttaa aataaaatct gtgattatct atcttttaat gaatgcctta   120
gatcattcac attaaagtga ttgttgttgt agttgtgttc atgtatacca tacttataac   180
tgttt                                                               185
```

<210> SEQ ID NO 60
<211> LENGTH: 163
<212> TYPE: DNA
<213> ORGANISM: Homo sapiens

<400> SEQUENCE: 60

```
gaattctact aaaactttag aaaagaaatt aacaccaatt ctcaaactat ttcagaaaat    60
tgaaaggag aagcctctcc caactaattc tatgaatcca gcattacccc ttaccaaaac   120
cagacaaaga tgaaacaaaa taataagaag aaggaactct ggg                    163
```

<210> SEQ ID NO 61
<211> LENGTH: 103
<212> TYPE: DNA
<213> ORGANISM: Homo sapiens
<220> FEATURE:
<221> NAME/KEY: modified_base
<222> LOCATION: (63)..(63)
<223> OTHER INFORMATION: a, c, t or g

<400> SEQUENCE: 61

```
attttccctg ctgggtgtgt ccagagatcc tttctggcta gtctgctagc actgcatgtg    60
tcnaccagca tctcaacctc acactagctg caacacttgg cca                    103
```

<210> SEQ ID NO 62
<211> LENGTH: 144
<212> TYPE: DNA
<213> ORGANISM: Homo sapiens
<220> FEATURE:
<221> NAME/KEY: modified_base
<222> LOCATION: (60)..(60)
<223> OTHER INFORMATION: a, c, t or g

<400> SEQUENCE: 62

```
cctctccaaa aagaaaatct ctgccattct atgtacactg gctgcatgaa gatgtatgtn    60
tatgaattag cctgcatgtc tgggtcccac cctgcacatg ctaacattcc tttccctccc   120
catacgagtc caaaaaaact atgc                                          144
```

<210> SEQ ID NO 63
<211> LENGTH: 173
<212> TYPE: DNA
<213> ORGANISM: Homo sapiens

```
<400> SEQUENCE: 63
tcagtcttca ggtgatattg aaatggaggc tgtaaggttt taataataca ggtttcaaaa    60
ccaggcagca acacatacta gccatgtaaa acttgagcta ccccaacccg cctggttgtt   120
gcttagtcct tctttgaaaa ttaaaattct gttctctgga aatagtattt agg          173

<210> SEQ ID NO 64
<211> LENGTH: 150
<212> TYPE: DNA
<213> ORGANISM: Homo sapiens

<400> SEQUENCE: 64
ttacaacctt tatgagattg gtgccattat caccattttc agacatgaaa aatacagcac    60
acacagttta agtaatatgc tgaattcctg cagcccgggg gatccactag ttctagagcg   120
gccgccaccg cggtggagct ccagcttttg                                    150

<210> SEQ ID NO 65
<211> LENGTH: 159
<212> TYPE: DNA
<213> ORGANISM: Homo sapiens

<400> SEQUENCE: 65
ccagtaactt ccttgtgttg tgtacattca actcacagag ttgaacgttc ccttagacag    60
agcagatttg aaacactctt tttgtgcaat tggcaagtgg agatttcaag cgctttaagg   120
tcaatggcag aaaaggaaat atcttcgttt caaaactag                          159

<210> SEQ ID NO 66
<211> LENGTH: 73
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t or g
<220> FEATURE:
<221> NAME/KEY: modified_base
<222> LOCATION: (64)..(64)
<223> OTHER INFORMATION: a, c, t or g

<400> SEQUENCE: 66
tcccaatcct tcctgtgact caagcntctg ctcattaggt atcctaggac aatattatgc    60
tgtntctatc aga                                                       73

<210> SEQ ID NO 67
<211> LENGTH: 87
<212> TYPE: DNA
<213> ORGANISM: Homo sapiens

<400> SEQUENCE: 67
agccagagcc aagctctctc actctgcaga gaagcctcag tctttagaag acagttcagc    60
tttatccaga attcctgcag ccggggg                                        87

<210> SEQ ID NO 68
<211> LENGTH: 110
<212> TYPE: DNA
<213> ORGANISM: Homo sapiens
<220> FEATURE:
<221> NAME/KEY: modified_base
<222> LOCATION: (104)..(104)
<223> OTHER INFORMATION: a, c, t or g
```

```
<400> SEQUENCE: 68
tatgatcaac aaatatatct tacaacatga gggtgcaata agatgagaaa ggttcgagag      60
tgtttatctt tagcaaatac atactatcgc gctcaaggta agtnttcaag               110

<210> SEQ ID NO 69
<211> LENGTH: 111
<212> TYPE: DNA
<213> ORGANISM: Homo sapiens
<220> FEATURE:
<221> NAME/KEY: modified_base
<222> LOCATION: (46)..(46)
<223> OTHER INFORMATION: a, c, t or g
<220> FEATURE:
<221> NAME/KEY: modified_base
<222> LOCATION: (50)..(50)
<223> OTHER INFORMATION: a, c, t or g

<400> SEQUENCE: 69
tattgtgccc agagataatt gtcctgcagt cagagcattc tatgtntttn tctgtcgttg      60
attaatcaag agggtttcag gcttccctgt aggaaaatgt ctaaagcata a              111

<210> SEQ ID NO 70
<211> LENGTH: 138
<212> TYPE: DNA
<213> ORGANISM: Homo sapiens
<220> FEATURE:
<221> NAME/KEY: modified_base
<222> LOCATION: (80)..(80)
<223> OTHER INFORMATION: a, c, t or g

<400> SEQUENCE: 70
attcatttat accctcattt attcatccaa cagccattca ataagcgtct gtgttcagcc      60
atgctctgac actgattgan ttcctgcagc cggggggatcc actagttcta gagcggccgc    120
accgaggtgg acgtcagc                                                  138

<210> SEQ ID NO 71
<211> LENGTH: 144
<212> TYPE: DNA
<213> ORGANISM: Homo sapiens

<400> SEQUENCE: 71
caggttgatg aagaaacgga tattagtgca atgaagaaca gctccgtctc tgtcagctgg      60 tcattttta tatgtcagag actgtcgaat ttcattgcg tttcaactaa ttacctcagt      120
ttgttaaaac tgaatatgaa ttcc                                           144

<210> SEQ ID NO 72
<211> LENGTH: 113
<212> TYPE: DNA
<213> ORGANISM: Homo sapiens
<220> FEATURE:
<221> NAME/KEY: modified_base
<222> LOCATION: (1)..(1)
<223> OTHER INFORMATION: a, c, t or g
<220> FEATURE:
<221> NAME/KEY: modified_base
<222> LOCATION: (24)..(24)
<223> OTHER INFORMATION: a, c, t or g

<400> SEQUENCE: 72
ntctatctag ttttatatga aganatcacg tatcacacga tggacccaaa gaggtccaaa      60
tatccacttg cagttctaca aaagagtgt ttcacaacag cactatcaag agg            113
```

```
<210> SEQ ID NO 73
<211> LENGTH: 97
<212> TYPE: DNA
<213> ORGANISM: Homo sapiens

<400> SEQUENCE: 73
tacattcttt ttcttaacta tccaccacct cccctcaaaa ttttaacagc atccagcctc    60
acaaaactca gatcttccct gtgtacagtt ccacttt                            97

<210> SEQ ID NO 74
<211> LENGTH: 143
<212> TYPE: DNA
<213> ORGANISM: Homo sapiens

<400> SEQUENCE: 74
gacaattcca ttcaatacca attgatgatg tttattttttg attccatttg atgatgatta   60
cattcgattc catttcatca tgattccatt cgattccact cgatgattcc attcgattcc   120
attcaatgat tattccactt gag                                          143

<210> SEQ ID NO 75
<211> LENGTH: 98
<212> TYPE: DNA
<213> ORGANISM: Homo sapiens
<220> FEATURE:
<221> NAME/KEY: modified_base
<222> LOCATION: (30)..(30)
<223> OTHER INFORMATION: a, c, t or g
<220> FEATURE:
<221> NAME/KEY: modified_base
<222> LOCATION: (42)..(42)
<223> OTHER INFORMATION: a, c, t or g
<220> FEATURE:
<221> NAME/KEY: modified_base
<222> LOCATION: (78)..(78)
<223> OTHER INFORMATION: a, c, t or g

<400> SEQUENCE: 75
aaatgataat atagtcaatt caggaaagan aatcatccta anatttcgta ttatgattag    60
aagtgtaatt tcgctganat agaaaatttc tcattatt                           98

<210> SEQ ID NO 76
<211> LENGTH: 88
<212> TYPE: DNA
<213> ORGANISM: Homo sapiens

<400> SEQUENCE: 76
agctgacatt gtaatttaat aaagctaagg ataaaacttc tgggtttttt gtttattgag    60
cccgctgact agaagagata agagatgg                                     88

<210> SEQ ID NO 77
<211> LENGTH: 101
<212> TYPE: DNA
<213> ORGANISM: Homo sapiens
<220> FEATURE:
<221> NAME/KEY: modified_base
<222> LOCATION: (23)..(23)
<223> OTHER INFORMATION: a, c, t or g
<220> FEATURE:
<221> NAME/KEY: modified_base
<222> LOCATION: (55)..(55)
<223> OTHER INFORMATION: a, c, t or g

<400> SEQUENCE: 77
ctctggttgt tgtcaggttt ttnattatta gattccagaa ttcctgcagc ccggnggatc    60
```
cactagttct agagcggccg ccaccgcggt ggagctccag c                           101

<210> SEQ ID NO 78
<211> LENGTH: 109
<212> TYPE: DNA
<213> ORGANISM: Homo sapiens

<400> SEQUENCE: 78
aaggttacag tgagctatga tccaccactg cactccagca tgggcaacaa agcgagaccc       60
agtatttaga tttatttgtt aatagccagg catattggta catgcgtgt                  109

<210> SEQ ID NO 79
<211> LENGTH: 121
<212> TYPE: DNA
<213> ORGANISM: Homo sapiens
<220> FEATURE:
<221> NAME/KEY: modified_base
<222> LOCATION: (61)..(61)
<223> OTHER INFORMATION: a, c, t or g

<400> SEQUENCE: 79
ctatatcaca tactttattg tcttgtacag tttgctttgt tcatgtgtg gatacccctga      60 nttcctgcag cccgggggat ccactagttc tagagcggcc gccaccgcgg tggagctcca     120
g                                                                    121

<210> SEQ ID NO 80
<211> LENGTH: 144
<212> TYPE: DNA
<213> ORGANISM: Homo sapiens
<220> FEATURE:
<221> NAME/KEY: modified_base
<222> LOCATION: (106)..(106)
<223> OTHER INFORMATION: a, c, t or g

<400> SEQUENCE: 80
ctatgagtgg cctccaagga gcattagatt agaaggtggc tggagggtgg atattttcat      60
acacagagac aaagctcccc atcccacaac agatccagag tctgtnttgg accacaggga    120
aggaaggccc ttctccagga ttct                                           144

<210> SEQ ID NO 81
<211> LENGTH: 160
<212> TYPE: DNA
<213> ORGANISM: Homo sapiens

<400> SEQUENCE: 81
ttaggagagg tcagagtggg ctggagcagc caggtgagcc tttgttgtgt aggcaggagg      60
aagaagcagt ggattttgag ttgaggacgg aatttgagag ggggagggaa aaggaaggga    120
atccgcagag gcagagctga ctgcactcgt gagggagggg                           160

<210> SEQ ID NO 82
<211> LENGTH: 164
<212> TYPE: DNA
<213> ORGANISM: Homo sapiens

<400> SEQUENCE: 82
atacaaattg cagactgcag cgttctgaga aacatctttg tgatgtttgt attcaggaca      60
gagagttgaa cattccctat catagagcag gttggaatca ctccttttgt agtatctgga    120
agtggacatt tggagcgctt tcaggcctat gttggaaaag gaaa                     164

<210> SEQ ID NO 83
<211> LENGTH: 164
<212> TYPE: DNA
<213> ORGANISM: Homo sapiens

<400> SEQUENCE: 83
ttgtggttct agattttatg gtctcttttt tattttttcat tttttgagac caagtttcac    60
tcttgttgcc cggctggagt gcagtgacgc gatcttggct caccgcaacc tctgcctcca   120
ggattcaagc gattcgcctg cctcagcctt actgagtagc tccc                     164

<210> SEQ ID NO 84
<211> LENGTH: 141
<212> TYPE: DNA
<213> ORGANISM: Homo sapiens
<220> FEATURE:
<221> NAME/KEY: modified_base
<222> LOCATION: (67)..(67)
<223> OTHER INFORMATION: a, c, t or g

<400> SEQUENCE: 84
tagttccagc tataccactt tctagccttc ttgattttgc tgaactgaga gtcagaagag    60
atatgtntct aggttatttc caatcattat gccatctcgg aagtggcagg ggtgctatac   120
tagactgaga caaataccc a                                               141

<210> SEQ ID NO 85
<211> LENGTH: 72
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t or g
<220> FEATURE:
<221> NAME/KEY: modified_base
<222> LOCATION: (42)..(42)
<223> OTHER INFORMATION: a, c, t or g

<400> SEQUENCE: 85
cttctaaaat tctatggtag tatganaggc tacacaaaag tntttggacc tgatacaaat    60
attataaatg at                                                         72

<210> SEQ ID NO 86
<211> LENGTH: 135
<212> TYPE: DNA
<213> ORGANISM: Homo sapiens

<400> SEQUENCE: 86
tcataaaata accattaata tttcactttc gttttttatc ctaaccttt tctaacacat     60 aaacatattc attgggaggt cgaggcgggc ggatcacgag gtaggagatc gacgaccatc   120
cggtaaaagg tgaaa                                                    135

<210> SEQ ID NO 87
<211> LENGTH: 107
<212> TYPE: DNA
<213> ORGANISM: Homo sapiens

<400> SEQUENCE: 87
cagccccaag aatgtctgga gcccgagtat catctggcag ccaccctcgg agaagggggg    60
gatccactag ttctagagcg gccgcaccgc ggtggagctc agctttt                 107

<210> SEQ ID NO 88

```
<211> LENGTH: 109
<212> TYPE: DNA
<213> ORGANISM: Homo sapiens

<400> SEQUENCE: 88
ccatgtggaa gcacagctat aaggctcttt ctatgaacca gaaagcaggc tttctctaaa    60
caccgaatct gccaatgcct tgatcttgga tttcccagat tccgaacta              109

<210> SEQ ID NO 89
<211> LENGTH: 112
<212> TYPE: DNA
<213> ORGANISM: Homo sapiens

<400> SEQUENCE: 89
cagggactta atcaacgcaa gcttatgacc cgcacttact gggaattcct cgttcatggg    60
gaataattgc aatccccgat ccccatcacg aatggggttc aacgggttac cc           112

<210> SEQ ID NO 90
<211> LENGTH: 125
<212> TYPE: DNA
<213> ORGANISM: Homo sapiens

<400> SEQUENCE: 90
acctgtaatc ccaactactc tggaggctga ggcaggagaa tggcatgaac ccgggaggtg    60
gaggatgcag tgagccaaga ttgtgccact gaactctagc ccaggcaaag gtgagagact   120
tgatc                                                              125

<210> SEQ ID NO 91
<211> LENGTH: 130
<212> TYPE: DNA
<213> ORGANISM: Homo sapiens
<220> FEATURE:
<221> NAME/KEY: modified_base
<222> LOCATION: (20)..(20)
<223> OTHER INFORMATION: a, c, t or g
<220> FEATURE:
<221> NAME/KEY: modified_base
<222> LOCATION: (56)..(56)
<223> OTHER INFORMATION: a, c, t or g
<220> FEATURE:
<221> NAME/KEY: modified_base
<222> LOCATION: (58)..(60)
<223> OTHER INFORMATION: a, c, t or g
<220> FEATURE:
<221> NAME/KEY: modified_base
<222> LOCATION: (75)..(75)
<223> OTHER INFORMATION: a, c, t or g
<220> FEATURE:
<221> NAME/KEY: modified_base
<222> LOCATION: (78)..(78)
<223> OTHER INFORMATION: a, c, t or g
<220> FEATURE:
<221> NAME/KEY: modified_base
<222> LOCATION: (100)..(100)
<223> OTHER INFORMATION: a, c, t or g

<400> SEQUENCE: 91
cacttaagat tgtatctttn actctatgag ttatttctca ataaaaagta aaattnannn    60
tactaataat taganatnat cttctctaga atgagcattn aatgagtcag ctagagaggc   120
gacttaactg                                                         130

<210> SEQ ID NO 92
<211> LENGTH: 104
<212> TYPE: DNA
<213> ORGANISM: Homo sapiens
```

```
<220> FEATURE:
<221> NAME/KEY: modified_base
<222> LOCATION: (81)..(81)
<223> OTHER INFORMATION: a, c, t or g
<220> FEATURE:
<221> NAME/KEY: modified_base
<222> LOCATION: (87)..(87)
<223> OTHER INFORMATION: a, c, t or g

<400> SEQUENCE: 92
cagcccttac attgtgtctg tgacccagtg ttaaatgaga cccaggtcaa gagacaactc    60
tttggctggt ctaggatatt ntataanata gatctatcac tctg                   104

<210> SEQ ID NO 93
<211> LENGTH: 122
<212> TYPE: DNA
<213> ORGANISM: Homo sapiens

<400> SEQUENCE: 93
cgtcagctca gcagcctgac aatttgaact cagtagtatc acattgccac atggctatgt   60
tcaggggtta atacttctta gcaaagaaat agagaccaat ctctgtgatc actttaaact  120
tt                                                                 122

<210> SEQ ID NO 94
<211> LENGTH: 76
<212> TYPE: DNA
<213> ORGANISM: Homo sapiens
<220> FEATURE:
<221> NAME/KEY: modified_base
<222> LOCATION: (50)..(51)
<223> OTHER INFORMATION: a, c, t or g

<400> SEQUENCE: 94
cacatggatg gggaggcctt ccaatcatgg cagaaggcaa aggagaaagn nagcacatct    60
tacaggcagc aggcaa                                                    76

<210> SEQ ID NO 95
<211> LENGTH: 109
<212> TYPE: DNA
<213> ORGANISM: Homo sapiens
<220> FEATURE:
<221> NAME/KEY: modified_base
<222> LOCATION: (24)..(24)
<223> OTHER INFORMATION: a, c, t or g
<220> FEATURE:
<221> NAME/KEY: modified_base
<222> LOCATION: (26)..(26)
<223> OTHER INFORMATION: a, c, t or g
<220> FEATURE:
<221> NAME/KEY: modified_base
<222> LOCATION: (28)..(28)
<223> OTHER INFORMATION: a, c, t or g
<220> FEATURE:
<221> NAME/KEY: modified_base
<222> LOCATION: (60)..(60)
<223> OTHER INFORMATION: a, c, t or g
<220> FEATURE:
<221> NAME/KEY: modified_base
<222> LOCATION: (68)..(68)
<223> OTHER INFORMATION: a, c, t or g
<220> FEATURE:
<221> NAME/KEY: modified_base
<222> LOCATION: (78)..(78)
<223> OTHER INFORMATION: a, c, t or g
<220> FEATURE:
<221> NAME/KEY: modified_base
<222> LOCATION: (100)..(101)
<223> OTHER INFORMATION: a, c, t or g
```

```
<400> SEQUENCE: 95
cagccccagc atggcaggaa tatntntngc attgggttct ttggaggagg aaagtacgtn      60
ctcagagnag gcaatttntc gccgctggtt taaggctttn natgaccga                109

<210> SEQ ID NO 96
<211> LENGTH: 148
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t or g
<220> FEATURE:
<221> NAME/KEY: modified_base
<222> LOCATION: (83)..(84)
<223> OTHER INFORMATION: a, c, t or g
<220> FEATURE:
<221> NAME/KEY: modified_base
<222> LOCATION: (86)..(86)
<223> OTHER INFORMATION: a, c, t or g
<220> FEATURE:
<221> NAME/KEY: modified_base
<222> LOCATION: (88)..(88)
<223> OTHER INFORMATION: a, c, t or g

<400> SEQUENCE: 96
cagccccgaa ttatgtatta anagttatcc tcaccaagaa agacaaggtt tctgtagttc      60
tctaacatca tatccctata tanntntnac tgtgcagtat ccagacaatg acactccttc     120
agagagaatt ctatggccac atctctaa                                       148

<210> SEQ ID NO 97
<211> LENGTH: 122
<212> TYPE: DNA
<213> ORGANISM: Homo sapiens
<220> FEATURE:
<221> NAME/KEY: modified_base
<222> LOCATION: (41)..(42)
<223> OTHER INFORMATION: a, c, t or g
<220> FEATURE:
<221> NAME/KEY: modified_base
<222> LOCATION: (48)..(51)
<223> OTHER INFORMATION: a, c, t or g
<220> FEATURE:
<221> NAME/KEY: modified_base
<222> LOCATION: (54)..(54)
<223> OTHER INFORMATION: a, c, t or g
<220> FEATURE:
<221> NAME/KEY: modified_base
<222> LOCATION: (110)..(110)
<223> OTHER INFORMATION: a, c, t or g

<400> SEQUENCE: 97
taaaactttg ttataagaga tggaagggtt taaatatata nntctaannn nttntagttt      60
aaagaattcc aaacttaaac atcttcagta gacttgacat tgtatttcgn atatcctatg    120
tc                                                                   122

<210> SEQ ID NO 98
<211> LENGTH: 88
<212> TYPE: DNA
<213> ORGANISM: Homo sapiens
<220> FEATURE:
<221> NAME/KEY: modified_base
<222> LOCATION: (38)..(46)
<223> OTHER INFORMATION: a, c, t or g

<400> SEQUENCE: 98
ctttaaattt ataaactcca aggcagtaca agtctggnnn nnnnnnagct acccaatatc      60
```

```
tgataaatat gaatacctaa taatagac                                              88
```

<210> SEQ ID NO 99
<211> LENGTH: 105
<212> TYPE: DNA
<213> ORGANISM: Homo sapiens

<400> SEQUENCE: 99

```
tcctaaaact ctccctcacc agcatcccaa tttaaagcct tggtccttgc tcctccctct          60 aggggggatcc actagttcta gagcggccgc caccgcggtg gagct                         105
```

<210> SEQ ID NO 100
<211> LENGTH: 86
<212> TYPE: DNA
<213> ORGANISM: Homo sapiens
<220> FEATURE:
<221> NAME/KEY: modified_base
<222> LOCATION: (22)..(25)
<223> OTHER INFORMATION: a, c, t or g
<220> FEATURE:
<221> NAME/KEY: modified_base
<222> LOCATION: (27)..(27)
<223> OTHER INFORMATION: a, c, t or g
<220> FEATURE:
<221> NAME/KEY: modified_base
<222> LOCATION: (74)..(74)
<223> OTHER INFORMATION: a, c, t or g
<220> FEATURE:
<221> NAME/KEY: modified_base
<222> LOCATION: (76)..(76)
<223> OTHER INFORMATION: a, c, t or g

<400> SEQUENCE: 100

```
cgccactatg ctcagctact tnnnntntgt tttgtagaga tgggtgtttc accatgttgc          60
ccagactgat cttnanctcc tgggtc                                               86
```

<210> SEQ ID NO 101
<211> LENGTH: 156
<212> TYPE: DNA
<213> ORGANISM: Homo sapiens
<220> FEATURE:
<221> NAME/KEY: modified_base
<222> LOCATION: (17)..(17)
<223> OTHER INFORMATION: a, c, t or g
<220> FEATURE:
<221> NAME/KEY: modified_base
<222> LOCATION: (49)..(49)
<223> OTHER INFORMATION: a, c, t or g

<400> SEQUENCE: 101

```
gaccctccac tgatttncca tcttgaccac tgcctaccca attactgtnc cagtcgaaac          60
ctgggcgcca tgtgacgact ctctccctct ctacagctac acaaccgccg tgtgctgtcg         120
ggtcttatcc tttccaccca gtccatggct tggtct                                   156
```

<210> SEQ ID NO 102
<211> LENGTH: 173
<212> TYPE: DNA
<213> ORGANISM: Homo sapiens
<220> FEATURE:
<221> NAME/KEY: modified_base
<222> LOCATION: (41)..(41)
<223> OTHER INFORMATION: a, c, t or g

<400> SEQUENCE: 102

```
cagccccata aaattaacca tcacactagg tgatgtcttt nttttttgag agcaagtctt          60
```

```
gctcgtcacc aggctggaat actgtggtgg gatctcagct cactgcacct ccacctcctg    120
ggttccagca attgttctgc ctcagcctgg gggatccact agttctagag cgg           173
```

<210> SEQ ID NO 103
<211> LENGTH: 191
<212> TYPE: DNA
<213> ORGANISM: Homo sapiens

<400> SEQUENCE: 103

```
cagccccctt agaaatagct cttcgagaca ctcctggtag acatgatccc aggcttgctg     60
agcagctgtg caaccatgcc tcaggcctga ggaacagctc gcaggccact ctgtctggta    120 atacccagg ccggccaagc aatagatctg catcccaggg ggatccacta gttctagagc    180
ggccgccacc g                                                         191
```

<210> SEQ ID NO 104
<211> LENGTH: 191
<212> TYPE: DNA
<213> ORGANISM: Homo sapiens
<220> FEATURE:
<221> NAME/KEY: modified_base
<222> LOCATION: (74)..(74)
<223> OTHER INFORMATION: a, c, t or g

<400> SEQUENCE: 104

```
gagccccctt ggctcagtct ggaaaggcaa gacaactaga aggtgggggg cttccagggc     60
ataggtagat tcanaaatgt actgattggc acttccttga ccgagttatt aactaaagac    120
ctggaatcaa tagaaaggaa tgtctgggtt aaggtaaggg ctatggggga tccactagtt    180
ctagacggcc g                                                         191
```

<210> SEQ ID NO 105
<211> LENGTH: 103
<212> TYPE: DNA
<213> ORGANISM: Homo sapiens
<220> FEATURE:
<221> NAME/KEY: modified_base
<222> LOCATION: (5)..(5)
<223> OTHER INFORMATION: a, c, t or g
<220> FEATURE:
<221> NAME/KEY: modified_base
<222> LOCATION: (9)..(9)
<223> OTHER INFORMATION: a, c, t or g
<220> FEATURE:
<221> NAME/KEY: modified_base
<222> LOCATION: (14)..(14)
<223> OTHER INFORMATION: a, c, t or g
<220> FEATURE:
<221> NAME/KEY: modified_base
<222> LOCATION: (21)..(21)
<223> OTHER INFORMATION: a, c, t or g
<220> FEATURE:
<221> NAME/KEY: modified_base
<222> LOCATION: (35)..(35)
<223> OTHER INFORMATION: a, c, t or g
<220> FEATURE:
<221> NAME/KEY: modified_base
<222> LOCATION: (44)..(44)
<223> OTHER INFORMATION: a, c, t or g
<220> FEATURE:
<221> NAME/KEY: modified_base
<222> LOCATION: (67)..(67)
<223> OTHER INFORMATION: a, c, t or g
<220> FEATURE:
<221> NAME/KEY: modified_base
<222> LOCATION: (71)..(71)
<223> OTHER INFORMATION: a, c, t or g
<220> FEATURE:
<221> NAME/KEY: modified_base
<222> LOCATION: (84)..(84)
<223> OTHER INFORMATION: a, c, t or g

<400> SEQUENCE: 105
ttctnagana tttnacatca nattaaccca ctganaaact tgcnaactct cactttcaac    60
gtctgancgg naatttttaat tggnggatcc actagttcta gag                    103

<210> SEQ ID NO 106
<211> LENGTH: 120
<212> TYPE: DNA
<213> ORGANISM: Homo sapiens
<220> FEATURE:
<221> NAME/KEY: modified_base
<222> LOCATION: (44)..(44)
<223> OTHER INFORMATION: a, c, t or g
<220> FEATURE:
<221> NAME/KEY: modified_base
<222> LOCATION: (73)..(73)
<223> OTHER INFORMATION: a, c, t or g

<400> SEQUENCE: 106
cagccccctt attaactcac cccttgcatt tgttcaaccc tagntaataa agtcactcag    60
gtgtacttct ganaattgaa gttaaatatt tttcaccaca gagctgaacc attacagagg   120

<210> SEQ ID NO 107
<211> LENGTH: 111
<212> TYPE: DNA
<213> ORGANISM: Homo sapiens
<220> FEATURE:
<221> NAME/KEY: modified_base
<222> LOCATION: (7)..(7)
<223> OTHER INFORMATION: a, c, t or g
<220> FEATURE:
<221> NAME/KEY: modified_base
<222> LOCATION: (22)..(26)
<223> OTHER INFORMATION: a, c, t or g
<220> FEATURE:
<221> NAME/KEY: modified_base
<222> LOCATION: (28)..(36)
<223> OTHER INFORMATION: a, c, t or g

<400> SEQUENCE: 107
tcataanata accattaata tnnnnntnnn nnnnnnatcc taacattttt ctaacacata    60
aacatattca cttgggaggc cgaggcgggc ggatcacgag gtcaggagat c             111

<210> SEQ ID NO 108
<211> LENGTH: 70
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t or g
<220> FEATURE:
<221> NAME/KEY: modified_base
<222> LOCATION: (31)..(31)
<223> OTHER INFORMATION: a, c, t or g
<220> FEATURE:
<221> NAME/KEY: modified_base
<222> LOCATION: (37)..(37)
<223> OTHER INFORMATION: a, c, t or g
<220> FEATURE:
<221> NAME/KEY: modified_base
<222> LOCATION: (39)..(39)
<223> OTHER INFORMATION: a, c, t or g
<220> FEATURE:
<221> NAME/KEY: modified_base
<222> LOCATION: (44)..(44)
<223> OTHER INFORMATION: a, c, t or g
<220> FEATURE:

<221> NAME/KEY: modified_base
<222> LOCATION: (59)..(59)
<223> OTHER INFORMATION: a, c, t or g
<220> FEATURE:
<221> NAME/KEY: modified_base
<222> LOCATION: (62)..(62)
<223> OTHER INFORMATION: a, c, t or g

<400> SEQUENCE: 108
caatttacac tctggcaggg ggaganagga naatttntnc tgtnggaagg gggagttgng    60 gnaggaggcc                                                          70

<210> SEQ ID NO 109
<211> LENGTH: 104
<212> TYPE: DNA
<213> ORGANISM: Homo sapiens
<220> FEATURE:
<221> NAME/KEY: modified_base
<222> LOCATION: (5)..(5)
<223> OTHER INFORMATION: a, c, t or g
<220> FEATURE:
<221> NAME/KEY: modified_base
<222> LOCATION: (11)..(11)
<223> OTHER INFORMATION: a, c, t or g
<220> FEATURE:
<221> NAME/KEY: modified_base
<222> LOCATION: (20)..(20)
<223> OTHER INFORMATION: a, c, t or g
<220> FEATURE:
<221> NAME/KEY: modified_base
<222> LOCATION: (28)..(28)
<223> OTHER INFORMATION: a, c, t or g
<220> FEATURE:
<221> NAME/KEY: modified_base
<222> LOCATION: (61)..(61)
<223> OTHER INFORMATION: a, c, t or g
<220> FEATURE:
<221> NAME/KEY: modified_base
<222> LOCATION: (69)..(69)
<223> OTHER INFORMATION: a, c, t or g
<220> FEATURE:
<221> NAME/KEY: modified_base
<222> LOCATION: (73)..(73)
<223> OTHER INFORMATION: a, c, t or g
<220> FEATURE:
<221> NAME/KEY: modified_base
<222> LOCATION: (75)..(75)
<223> OTHER INFORMATION: a, c, t or g
<220> FEATURE:
<221> NAME/KEY: modified_base
<222> LOCATION: (95)..(95)
<223> OTHER INFORMATION: a, c, t or g

<400> SEQUENCE: 109
caaanactaa natacctctn agtctggnta gacactttca ctggataggt agaggccttt    60
nctacaggnt atnanaaggc caccacagtc atttnttccc ttct                   104

<210> SEQ ID NO 110
<211> LENGTH: 68
<212> TYPE: DNA
<213> ORGANISM: Homo sapiens
<220> FEATURE:
<221> NAME/KEY: modified_base
<222> LOCATION: (13)..(13)
<223> OTHER INFORMATION: a, c, t or g
<220> FEATURE:
<221> NAME/KEY: modified_base
<222> LOCATION: (25)..(26)
<223> OTHER INFORMATION: a, c, t or g
<220> FEATURE:
<221> NAME/KEY: modified_base
<222> LOCATION: (36)..(36)
<223> OTHER INFORMATION: a, c, t or g

```
<220> FEATURE:
<221> NAME/KEY: modified_base
<222> LOCATION: (40)..(40)
<223> OTHER INFORMATION: a, c, t or g
<220> FEATURE:
<221> NAME/KEY: modified_base
<222> LOCATION: (51)..(55)
<223> OTHER INFORMATION: a, c, t or g
<220> FEATURE:
<221> NAME/KEY: modified_base
<222> LOCATION: (57)..(57)
<223> OTHER INFORMATION: a, c, t or g

<400> SEQUENCE: 110
tcatgtaggc ctnttcacga ttttnnaaat catttnagtn acatccaagt nnnnntngct    60
gttaatca                                                              68

<210> SEQ ID NO 111
<211> LENGTH: 107
<212> TYPE: DNA
<213> ORGANISM: Homo sapiens
<220> FEATURE:
<221> NAME/KEY: modified_base
<222> LOCATION: (43)..(44)
<223> OTHER INFORMATION: a, c, t or g

<400> SEQUENCE: 111
cagccccaat caagggctgt ttctcaatct ctttgtataa aannctagat tctgtattag    60
tctgttctca ggctgctaat aaagacatac ccaaggctgc gtacttt                  107

<210> SEQ ID NO 112
<211> LENGTH: 111
<212> TYPE: DNA
<213> ORGANISM: Homo sapiens

<400> SEQUENCE: 112
tggaaagaaa aactatgtac atctgagacg ctgcagctgg tatcctactt ctttcagagc    60
atcaacaggt taagtgtgga ttcatccaca ccctcagacc cgtgaccgta g             111

<210> SEQ ID NO 113
<211> LENGTH: 121
<212> TYPE: DNA
<213> ORGANISM: Homo sapiens

<400> SEQUENCE: 113
gaatctctac accaaccctc tcttaacctc tacagttcaa atccaaatct caaactttct    60
gatttgaatt tgcttatccc tatgtaattc taacttaaga cctaagacca aagggaatc   120 c                                                                   121

<210> SEQ ID NO 114
<211> LENGTH: 103
<212> TYPE: DNA
<213> ORGANISM: Homo sapiens
<220> FEATURE:
<221> NAME/KEY: modified_base
<222> LOCATION: (60)..(60)
<223> OTHER INFORMATION: a, c, t or g

<400> SEQUENCE: 114
tcttccagct aaatagttgc agagtcagag tagaagccag ctctcctgac aatatatttn    60
atgatattct agagaatatc cctagaatca ttcctaggta ctc                     103

<210> SEQ ID NO 115
```

<211> LENGTH: 86
<212> TYPE: DNA
<213> ORGANISM: Homo sapiens
<220> FEATURE:
<221> NAME/KEY: modified_base
<222> LOCATION: (41)..(41)
<223> OTHER INFORMATION: a, c, t or g
<220> FEATURE:
<221> NAME/KEY: modified_base
<222> LOCATION: (44)..(45)
<223> OTHER INFORMATION: a, c, t or g

<400> SEQUENCE: 115
tgtcattggt aatttatgtg agaacacaaa gcatccaaca ntanntgatt ctgcatttcg    60
accaacagat agtttctcat cgaaga                                        86

<210> SEQ ID NO 116
<211> LENGTH: 120
<212> TYPE: DNA
<213> ORGANISM: Homo sapiens
<220> FEATURE:
<221> NAME/KEY: modified_base
<222> LOCATION: (23)..(23)
<223> OTHER INFORMATION: a, c, t or g
<220> FEATURE:
<221> NAME/KEY: modified_base
<222> LOCATION: (30)..(30)
<223> OTHER INFORMATION: a, c, t or g
<220> FEATURE:
<221> NAME/KEY: modified_base
<222> LOCATION: (47)..(47)
<223> OTHER INFORMATION: a, c, t or g
<220> FEATURE:
<221> NAME/KEY: modified_base
<222> LOCATION: (50)..(50)
<223> OTHER INFORMATION: a, c, t or g
<220> FEATURE:
<221> NAME/KEY: modified_base
<222> LOCATION: (74)..(74)
<223> OTHER INFORMATION: a, c, t or g
<220> FEATURE:
<221> NAME/KEY: modified_base
<222> LOCATION: (79)..(79)
<223> OTHER INFORMATION: a, c, t or g
<220> FEATURE:
<221> NAME/KEY: modified_base
<222> LOCATION: (93)..(93)
<223> OTHER INFORMATION: a, c, t or g

<400> SEQUENCE: 116
cagccccgtt tgtttttacct ttngcttttn atgtgcttct ctaacanttn agggcgaact    60
aaccagcatg aggnttgtnt ctgcttgatt ttnaaccatc ctttcctgtc tgtacacagg   120

<210> SEQ ID NO 117
<211> LENGTH: 95
<212> TYPE: DNA
<213> ORGANISM: Homo sapiens
<220> FEATURE:
<221> NAME/KEY: modified_base
<222> LOCATION: (15)..(15)
<223> OTHER INFORMATION: a, c, t or g
<220> FEATURE:
<221> NAME/KEY: modified_base
<222> LOCATION: (17)..(17)
<223> OTHER INFORMATION: a, c, t or g
<220> FEATURE:
<221> NAME/KEY: modified_base
<222> LOCATION: (43)..(43)
<223> OTHER INFORMATION: a, c, t or g
<220> FEATURE:
<221> NAME/KEY: modified_base
<222> LOCATION: (45)..(45)
<223> OTHER INFORMATION: a, c, t or g

```
<220> FEATURE:
<221> NAME/KEY: modified_base
<222> LOCATION: (74)..(74)
<223> OTHER INFORMATION: a, c, t or g
<220> FEATURE:
<221> NAME/KEY: modified_base
<222> LOCATION: (79)..(79)
<223> OTHER INFORMATION: a, c, t or g
<220> FEATURE:
<221> NAME/KEY: modified_base
<222> LOCATION: (81)..(81)
<223> OTHER INFORMATION: a, c, t or g

<400> SEQUENCE: 117
ccctccctga gtctntntaa cagcagcact gcccccaaac ctnanttggt tcccctgata      60
gccaggtacc cggnttctnt ngcagtgcta actgt                                95

<210> SEQ ID NO 118
<211> LENGTH: 109
<212> TYPE: DNA
<213> ORGANISM: Homo sapiens
<220> FEATURE:
<221> NAME/KEY: modified_base
<222> LOCATION: (7)..(11)
<223> OTHER INFORMATION: a, c, t or g
<220> FEATURE:
<221> NAME/KEY: modified_base
<222> LOCATION: (19)..(19)
<223> OTHER INFORMATION: a, c, t or g
<220> FEATURE:
<221> NAME/KEY: modified_base
<222> LOCATION: (26)..(26)
<223> OTHER INFORMATION: a, c, t or g
<220> FEATURE:
<221> NAME/KEY: modified_base
<222> LOCATION: (28)..(28)
<223> OTHER INFORMATION: a, c, t or g
<220> FEATURE:
<221> NAME/KEY: modified_base
<222> LOCATION: (31)..(31)
<223> OTHER INFORMATION: a, c, t or g
<220> FEATURE:
<221> NAME/KEY: modified_base
<222> LOCATION: (72)..(72)
<223> OTHER INFORMATION: a, c, t or g
<220> FEATURE:
<221> NAME/KEY: modified_base
<222> LOCATION: (78)..(78)
<223> OTHER INFORMATION: a, c, t or g
<220> FEATURE:
<221> NAME/KEY: modified_base
<222> LOCATION: (86)..(86)
<223> OTHER INFORMATION: a, c, t or g

<400> SEQUENCE: 118
tattaannnn nctaatctna atattntngt ntctcgggga acagaaaagc ctgaggagaa      60
ggagagatag tnggaatntc tagttnttgg agcagtcaga acacacata                 109

<210> SEQ ID NO 119
<211> LENGTH: 79
<212> TYPE: DNA
<213> ORGANISM: Homo sapiens
<220> FEATURE:
<221> NAME/KEY: modified_base
<222> LOCATION: (68)..(73)
<223> OTHER INFORMATION: a, c, t or g

<400> SEQUENCE: 119
cctgtattac agaaccaagg attaaaaact cagcagatgt gtaatgagtt ttaaataatt      60
acaatatnnn nnntataaa                                                  79
```

<210> SEQ ID NO 120
<211> LENGTH: 83
<212> TYPE: DNA
<213> ORGANISM: Homo sapiens
<220> FEATURE:
<221> NAME/KEY: modified_base
<222> LOCATION: (12)..(13)
<223> OTHER INFORMATION: a, c, t or g
<220> FEATURE:
<221> NAME/KEY: modified_base
<222> LOCATION: (32)..(33)
<223> OTHER INFORMATION: a, c, t or g
<220> FEATURE:
<221> NAME/KEY: modified_base
<222> LOCATION: (42)..(43)
<223> OTHER INFORMATION: a, c, t or g
<220> FEATURE:
<221> NAME/KEY: modified_base
<222> LOCATION: (49)..(49)
<223> OTHER INFORMATION: a, c, t or g

<400> SEQUENCE: 120
tagttgatcc gnnagcccat gcgataccgc gnnggcgctc gnngccgang ggggatccac      60
tagttctaga gcggccgcca ccg                                              83

<210> SEQ ID NO 121
<211> LENGTH: 177
<212> TYPE: DNA
<213> ORGANISM: Homo sapiens

<400> SEQUENCE: 121
cgtttgtttt acctttcact tttaatgtgc tttctctaac aattaagggc gaactaacca      60
gcatgaggat tgtgtctgct tgattttaaa ccatccttta atgtctgtac acaggaaatg     120
ttatcaacaa gagatgattc ttgggggatc cactaggttc tagagcggcc gccaccg        177

<210> SEQ ID NO 122
<211> LENGTH: 103
<212> TYPE: DNA
<213> ORGANISM: Homo sapiens
<220> FEATURE:
<221> NAME/KEY: modified_base
<222> LOCATION: (12)..(12)
<223> OTHER INFORMATION: a, c, t or g
<220> FEATURE:
<221> NAME/KEY: modified_base
<222> LOCATION: (16)..(16)
<223> OTHER INFORMATION: a, c, t or g
<220> FEATURE:
<221> NAME/KEY: modified_base
<222> LOCATION: (62)..(62)
<223> OTHER INFORMATION: a, c, t or g

<400> SEQUENCE: 122
ttatagttta anacanagat ggtaacagcc ctttcccaaa gcagacctcc ttcttgcctg      60
gnaaagggct gttaccatct ttgttttaaa ctataaacta taa                      103

<210> SEQ ID NO 123
<211> LENGTH: 139
<212> TYPE: DNA
<213> ORGANISM: Homo sapiens
<220> FEATURE:
<221> NAME/KEY: modified_base
<222> LOCATION: (24)..(24)
<223> OTHER INFORMATION: a, c, t or g
<220> FEATURE:
<221> NAME/KEY: modified_base
<222> LOCATION: (92)..(92)
<223> OTHER INFORMATION: a, c, t or g

<400> SEQUENCE: 123
caagaagggt ggtgctggca tttncttctg gtgagggcct caggaagctt tcaatcatgg     60
cagaaagtga gaggagagta ggcatgtcac anagagagac atgccttcat tctcggggga    120
tccactagtt ctagagcgg                                                  139

<210> SEQ ID NO 124
<211> LENGTH: 103
<212> TYPE: DNA
<213> ORGANISM: Homo sapiens
<220> FEATURE:
<221> NAME/KEY: modified_base
<222> LOCATION: (14)..(14)
<223> OTHER INFORMATION: a, c, t or g
<220> FEATURE:
<221> NAME/KEY: modified_base
<222> LOCATION: (26)..(26)
<223> OTHER INFORMATION: a, c, t or g
<220> FEATURE:
<221> NAME/KEY: modified_base
<222> LOCATION: (57)..(57)
<223> OTHER INFORMATION: a, c, t or g
<220> FEATURE:
<221> NAME/KEY: modified_base
<222> LOCATION: (70)..(71)
<223> OTHER INFORMATION: a, c, t or g

<400> SEQUENCE: 124
cattaaagcc tttnttagga aatctnttta aacaacagaa taaaagggat gactttnaga     60
tagaactttn ngtgacatct ccagtttctg gttacatgat att                      103

<210> SEQ ID NO 125
<211> LENGTH: 103
<212> TYPE: DNA
<213> ORGANISM: Homo sapiens
<220> FEATURE:
<221> NAME/KEY: modified_base
<222> LOCATION: (17)..(17)
<223> OTHER INFORMATION: a, c, t or g
<220> FEATURE:
<221> NAME/KEY: modified_base
<222> LOCATION: (22)..(22)
<223> OTHER INFORMATION: a, c, t or g
<220> FEATURE:
<221> NAME/KEY: modified_base
<222> LOCATION: (42)..(42)
<223> OTHER INFORMATION: a, c, t or g
<220> FEATURE:
<221> NAME/KEY: modified_base
<222> LOCATION: (78)..(78)
<223> OTHER INFORMATION: a, c, t or g
<220> FEATURE:
<221> NAME/KEY: modified_base
<222> LOCATION: (96)..(98)
<223> OTHER INFORMATION: a, c, t or g

<400> SEQUENCE: 125
cagagagaga gaaacanaca gncagagaga gagagaccac anagagagag agagagagaa     60
gatcagacag agaaaganag agacagagac agacannnag aca                      103

<210> SEQ ID NO 126
<211> LENGTH: 113
<212> TYPE: DNA
<213> ORGANISM: Homo sapiens
<220> FEATURE:
<221> NAME/KEY: modified_base
<222> LOCATION: (29)..(29)
<223> OTHER INFORMATION: a, c, t or g
<220> FEATURE:

<221> NAME/KEY: modified_base
<222> LOCATION: (101)..(101)
<223> OTHER INFORMATION: a, c, t or g
<220> FEATURE:
<221> NAME/KEY: modified_base
<222> LOCATION: (103)..(103)
<223> OTHER INFORMATION: a, c, t or g

<400> SEQUENCE: 126
cagccccaga gagagagaaa cagacaggna gagagagaga gacacagaga gagagagaga    60
gagaagatca gacagagaaa gagagagaca gagacagaca nanagaatag aga           113

<210> SEQ ID NO 127
<211> LENGTH: 181
<212> TYPE: DNA
<213> ORGANISM: Homo sapiens

<400> SEQUENCE: 127
actcatttta tgaggccaga atcatcctga taccaaaacc tggcagagac acacacacac    60
aaaagaaaat ttcaggccaa tatccctgat aaacattgat gcaaaaatcc tcaataaaat    120
actggcaaac tgaatccagt agcacatcaa aaagctgggg gatccactag ttctagagcg    180
g                                                                    181

<210> SEQ ID NO 128
<211> LENGTH: 150
<212> TYPE: DNA
<213> ORGANISM: Homo sapiens

<400> SEQUENCE: 128
cccgccccat gtagctctca ggtggcccat gacaccacac tgttcttcct tcctctccat    60
gggtcacacc ggccacctag tcagtcctaa cgtcggaacc tggatacctc cattgctggt    120
gctggacccg tcactgtttt ggatattttc                                     150

<210> SEQ ID NO 129
<211> LENGTH: 173
<212> TYPE: DNA
<213> ORGANISM: Homo sapiens

<400> SEQUENCE: 129
tcctaagtgt cccaacagtg gagcacatta ttcaggaact taaagatata atcgcagaac    60
agcacctcca agctcgtaaa tgcttatctc ggtaaccctc agtcatggga caatcaaatt    120
caatacatcg gaggaacacc atgctgacgg gggatccact agttctagag cgg           173

<210> SEQ ID NO 130
<211> LENGTH: 187
<212> TYPE: DNA
<213> ORGANISM: Homo sapiens
<220> FEATURE:
<221> NAME/KEY: modified_base
<222> LOCATION: (23)..(24)
<223> OTHER INFORMATION: a, c, t or g
<220> FEATURE:
<221> NAME/KEY: modified_base
<222> LOCATION: (31)..(32)
<223> OTHER INFORMATION: a, c, t or g

<400> SEQUENCE: 130
ctatagaagc tccttctata ttnngcttat nncactcatg gcggtagttt gaattcagat    60
ctctgggtca tttattatcc atggaaagtt aatttgagat gttggaactt ttaaacagtg    120
tttgtttatt gtgctaatca cgatctgtta ctaaatttga ttgggggatc cactagttct    180
agagcgg                                                             187

<210> SEQ ID NO 131
<211> LENGTH: 170
<212> TYPE: DNA
<213> ORGANISM: Homo sapiens

<400> SEQUENCE: 131
cagatatttg tagatatgcc gcgttatttc tgagggctct gttctgttcc attgatctat    60
atctctgtct ttggtaccag taccatgctg ttttggttac tgtagccttg tagtatagtt   120
tgaagtcagg tagcatgatg cctccggggg atccactagt tctagagcgg              170

<210> SEQ ID NO 132
<211> LENGTH: 147
<212> TYPE: DNA
<213> ORGANISM: Homo sapiens
<220> FEATURE:
<221> NAME/KEY: modified_base
<222> LOCATION: (69)..(79)
<223> OTHER INFORMATION: a, c, t or g
<220> FEATURE:
<221> NAME/KEY: modified_base
<222> LOCATION: (83)..(83)
<223> OTHER INFORMATION: a, c, t or g

<400> SEQUENCE: 132
tctctaaaat tctatggtag ttgaaaggct acacaaaagt ttttggacct gatacaaata    60
ttataaatnn nnnnnnnnnt gtntgatttg atactccatg taaaactctt cctaatggtc   120 tcggggatc cactagttct agagcgg                                        147

<210> SEQ ID NO 133
<211> LENGTH: 123
<212> TYPE: DNA
<213> ORGANISM: Homo sapiens

<400> SEQUENCE: 133
tattaaaaat acaaaaaatt agccgggagt ggtggcacgc gcctgtagtc ccagctactc    60
gggaggctat ggcaggaaaa tcccttgaac ctgggaggcg aagttgcag cgagaagaga   120 tca                                                                 123

<210> SEQ ID NO 134
<211> LENGTH: 164
<212> TYPE: DNA
<213> ORGANISM: Homo sapiens

<400> SEQUENCE: 134
ctgtctttca agtttcaggc ttgaaagtga aaataatgc ataatttacg gaagctattg    60
gtgtgaaaat atccaagaga agaatgagga atagtggagt gaaataaaca ggagattagg   120
tagatagaaa ttgactattg ggggatccac tagttctaga gcgg                    164

<210> SEQ ID NO 135
<211> LENGTH: 193
<212> TYPE: DNA
<213> ORGANISM: Homo sapiens
<220> FEATURE:
<221> NAME/KEY: modified_base
<222> LOCATION: (60)..(60)
<223> OTHER INFORMATION: a, c, t or g
<220> FEATURE:
<221> NAME/KEY: modified_base
<222> LOCATION: (64)..(64)

<223> OTHER INFORMATION: a, c, t or g
<220> FEATURE:
<221> NAME/KEY: modified_base
<222> LOCATION: (113)..(113)
<223> OTHER INFORMATION: a, c, t or g

<400> SEQUENCE: 135

| | | | | | |
|---|---|---|---|---|---|
| cttaatatgg | tatgcttaat | gtagtgagct | aaacaaaata | acaatgtgta | tagtattgtn | 60 |
| taanataccc | cacttccaat | tgtttaaagt | gcaaaacaaa | ttatatgttt | ganagttaag | 120 |
| gtggaataaa | tgaagattaa | atgatatgaa | ctactcagaa | aacaggtagg | gggatccact | 180 |
| agttctagag | cgg | | | | | 193 |

<210> SEQ ID NO 136
<211> LENGTH: 233
<212> TYPE: DNA
<213> ORGANISM: Homo sapiens

<400> SEQUENCE: 136

| | | | | | |
|---|---|---|---|---|---|
| cattgattaa | atttattgat | gcattgtaaa | tttgaatcaa | tatctattaa | tcccaagctg | 60 |
| gagtgcagtg | gcgccatctc | agctcactgc | gacctctgcc | tcccgggttc | aagcaattct | 120 |
| catacctcag | cctcccgagt | agctggaacc | acaggcatga | gccaccatgc | ccggctagtt | 180 |
| acagggtttt | cctatgctat | ccaggctgga | gtgcagtggg | ggatccacta | gtt | 233 |

<210> SEQ ID NO 137
<211> LENGTH: 194
<212> TYPE: DNA
<213> ORGANISM: Homo sapiens

<400> SEQUENCE: 137

| | | | | | |
|---|---|---|---|---|---|
| ctaaaggatc | cttcaactct | gtgagttgaa | tacacacaac | acaaggaagt | tactgagaat | 60 |
| tattctgtct | agcataatat | gaagaaatcc | cgtttccaac | tgaagacctc | aaagaggctg | 120 |
| aatatccact | tgcagacttt | acagagtgtt | tcctaactgc | tctatgagag | ggggatccac | 180 |
| tagttctaga | gcgg | | | | | 194 |

<210> SEQ ID NO 138
<211> LENGTH: 155
<212> TYPE: DNA
<213> ORGANISM: Homo sapiens

<400> SEQUENCE: 138

| | | | | | |
|---|---|---|---|---|---|
| cagcccggaa | aatatagggc | aaatttttt | attttgctgt | ttggtgactc | caccacttt | 60 |
| gcaacagtac | ttttggtgcc | cattaaccaa | attactttga | tttctttgtg | taaatattat | 120 |
| gaagaccaga | accttttgag | ggggatccac | tagtt | | | 155 |

<210> SEQ ID NO 139
<211> LENGTH: 200
<212> TYPE: DNA
<213> ORGANISM: Homo sapiens

<400> SEQUENCE: 139

| | | | | | |
|---|---|---|---|---|---|
| ctagacaaaa | gccccatcac | ctggatgaat | cagtgcagag | ttacgtcaca | aagtcctttt | 60 |
| aggcagatcc | tagacaaggg | ttacatcact | tggatgatca | gtgcagagat | atgtcacaat | 120 |
| gccactgtag | ggtgagccta | gaaaagagtt | tcatgaccta | ggtgatcagt | gcagagggg | 180 |
| atccactagt | tctagagcgg | | | | | 200 |

<210> SEQ ID NO 140
<211> LENGTH: 169
<212> TYPE: DNA
<213> ORGANISM: Homo sapiens

<400> SEQUENCE: 140
ctgtgactgt gcctatagaa gaaaaaaaaa atagcgtgta atctcagcac tctgggaggc      60
caaagcaggg gggatcactt gaggccaaga gttcaagacc agcctggcca acaaagcgaa     120
accttctctc tactaaaaat acaaaaatta gccgggcatg gtggcactc                169

<210> SEQ ID NO 141
<211> LENGTH: 211
<212> TYPE: DNA
<213> ORGANISM: Homo sapiens

<400> SEQUENCE: 141
agggccacca gctggtgaat cctgccccac cagctcagag ctcttcccat tcatggagta      60
tatcatagga gactggattt ccaaagctgc atggagcttc attcctgaac tggtcaccct     120
gtgtctagtc ttgttttctc aatccatcct gctctccagc agcctcaata cttctaaaat     180
tgtccggggg atccactagt tctagaggcg g                                    211

<210> SEQ ID NO 142
<211> LENGTH: 195
<212> TYPE: DNA
<213> ORGANISM: Homo sapiens

<400> SEQUENCE: 142
cacagacatc ctgtgccacc tcattcactc tcacatgcct ctgaggtgag ggggataaca      60
gcactagtat catttgatac tgatacaaat cggctctaaa tattgtgggg atgctggtgg     120
tgttattgct ggactccatt acacaagttt catgagccag tgaaaatcac tgtgggggat     180
ccactagttc tagag                                                     195

<210> SEQ ID NO 143
<211> LENGTH: 199
<212> TYPE: DNA
<213> ORGANISM: Homo sapiens

<400> SEQUENCE: 143
cagccctaaa gtataataaa aaaaaatttt ttaaagaatc ttcacaaaag aactctgaaa      60
tgtcagcatg agcagatgat gaagtatcat aggaatccat ttttgctgt atttcttatt     120 taatagagaa agaaatttca tatgctgtaa tatgtttcca attggaaatt aaaatctgat     180
aggggggatc cactagttc                                                  199

<210> SEQ ID NO 144
<211> LENGTH: 178
<212> TYPE: DNA
<213> ORGANISM: Homo sapiens

<400> SEQUENCE: 144 cagccccct gtaacaatat gggctgttct agctgtaatt cacctctgga gccatcagaa       60
tcctcctggt aaaaatggcc ctaatatcaa acacagaggc cactgctagt taaactttat     120
aaatcgaaca agaaatcata tgatataatc agataagagc ctgggggatc cactagtt      178

<210> SEQ ID NO 145
<211> LENGTH: 158
<212> TYPE: DNA

```
<213> ORGANISM: Homo sapiens
<220> FEATURE:
<221> NAME/KEY: modified_base
<222> LOCATION: (68)..(68)
<223> OTHER INFORMATION: a, c, t or g
<220> FEATURE:
<221> NAME/KEY: modified_base
<222> LOCATION: (74)..(74)
<223> OTHER INFORMATION: a, c, t or g

<400> SEQUENCE: 145 cagcccctg ggctcaagca atctgcccac ctcggcctcc ccaagtgctg ggattacagg      60
tgtgagtnac tgtncccggc cagccttgtc tatttgtcag aaacagggag ttggggcaac    120
cctggtgcca agatatgggg gggatccact agttctag                            158

<210> SEQ ID NO 146
<211> LENGTH: 184
<212> TYPE: DNA
<213> ORGANISM: Homo sapiens

<400> SEQUENCE: 146 cagccctgc taaataactt tcgaagttaa gaaagctaat ggtatatcat caggcaccaa      60
taaaactatc ttgagatttg acaatgccaa ctgaaaaatt tcttctgcaa ggcagagcca   120
gttacctttt ataatatcaa tttagattca cacaaagaca ttctcagggg gatccactag   180
ttct                                                                184

<210> SEQ ID NO 147
<211> LENGTH: 219
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t or g
<220> FEATURE:
<221> NAME/KEY: modified_base
<222> LOCATION: (32)..(32)
<223> OTHER INFORMATION: a, c, t or g
<220> FEATURE:
<221> NAME/KEY: modified_base
<222> LOCATION: (57)..(57)
<223> OTHER INFORMATION: a, c, t or g
<220> FEATURE:
<221> NAME/KEY: modified_base
<222> LOCATION: (117)..(118)
<223> OTHER INFORMATION: a, c, t or g

<400> SEQUENCE: 147
cagccccacg ggtggtaatc ntggctgctt tntgcacttc cacataaagt gcttctncta    60
cgctgtctcc actcagaaac aattacaaca gtatgtgaag cagtattgaa aacttcnnaa   120
gctgcacaca gattcattga aaagggcaga agcctcatta atactagagt ctgaggcaca   180
acctatgacc gaacactggg ggggatccac tagttctag                          219

<210> SEQ ID NO 148
<211> LENGTH: 185
<212> TYPE: DNA
<213> ORGANISM: Homo sapiens

<400> SEQUENCE: 148 cagccccag aaaaaaaaga gcaagaggat ggggctgaaa aaattactca agaaataat      60 ggctaaaaag tactcaggtt tatcaaaaga caagtctgca gaactaagaa gatgacaaaa   120
tccttgtcat agacagaatg tgtgtttccc aaacttcgtg tgttgggggg atccactagt   180
```

-continued tctag                                                          185

<210> SEQ ID NO 149
<211> LENGTH: 129
<212> TYPE: DNA
<213> ORGANISM: Homo sapiens

<400> SEQUENCE: 149
cagccctgca gtatttagtt ttctattcct gagttagttc acttaggaaa atggtctcta    60
gctccatcca tgaagcacca aatccctcca gcccagtagc aaggagacag aattttttact  120 ctgtctctg                                                          129

<210> SEQ ID NO 150
<211> LENGTH: 74
<212> TYPE: DNA
<213> ORGANISM: Homo sapiens
<220> FEATURE:
<221> NAME/KEY: modified_base
<222> LOCATION: (50)..(53)
<223> OTHER INFORMATION: a, c, t or g

<400> SEQUENCE: 150
cagcccctct tttctgctcc taaggaagat gcattctcag gatacaggan nnnggggga    60 tccactagtt catg                                                    74

<210> SEQ ID NO 151
<211> LENGTH: 95
<212> TYPE: DNA
<213> ORGANISM: Homo sapiens

<400> SEQUENCE: 151
cagccccatt taacctggag aggaataccc taaggattct tggaggctga aagacttaaa    60
atttgaggaa tgaaagaata gcaagggtga atcgg                              95

<210> SEQ ID NO 152
<211> LENGTH: 144
<212> TYPE: DNA
<213> ORGANISM: Homo sapiens

<400> SEQUENCE: 152
cagccctgca gtatttagtt ttctattcct gagttagttc acttaggaaa atggtctcta    60
gctccatcca tgaagcacca aatccctcca gcccagtagc aaggagacag aattttttact  120 ctgtctctga tgagaagagt gtac                                         144

<210> SEQ ID NO 153
<211> LENGTH: 138
<212> TYPE: DNA
<213> ORGANISM: Homo sapiens

<400> SEQUENCE: 153
cagccctgat agttacctta ctgttttgct atgaccatac tctacataga gtatttagat    60
taaatggagg aatgagaata tgagattagt ttctcatatt cttgtgatca tgacaggacc   120
tgagattctg cacagatg                                                138

<210> SEQ ID NO 154
<211> LENGTH: 139
<212> TYPE: DNA
<213> ORGANISM: Homo sapiens

```
<400> SEQUENCE: 154
cagccccgct gtttctaaag tcagtgtgtg tgtgtgtgtg tgtgtgtgtg tgtgtgagag      60
agagagagag agagagagcg tatgcatgtg tgtctgcatg tgtgtgtgcg cgcgtacatt     120
tgggagacgg tgtgtaagt                                                  139

<210> SEQ ID NO 155
<211> LENGTH: 133
<212> TYPE: DNA
<213> ORGANISM: Homo sapiens

<400> SEQUENCE: 155
cagcccggaa aggtaataca agtaagatga ttataaacaa atgctttaaa acagagtcaa      60
tgaaaccagt ctgtttgtga ggcccaaggc tccatatttt acaactcagt ctgtaaggat     120
agctatgtat ctg                                                        133
```